(12) United States Patent  
Weinstein et al.

(10) Patent No.: US 7,938,113 B2  
(45) Date of Patent: May 10, 2011

(54) INLINE VAPORIZER

(75) Inventors: Lawrence Alan Weinstein, Chesterfield, VA (US); Norman Hugh Tiffin, Chesterfield, VA (US); Tuan Quoc Tran, Glen Allen, VA (US); Drew E. Sunstein, Greenland, NH (US); Douglas H. Currie, Jr., Londonderry, NH (US); David E. Roche, Nashua, NH (US)

(73) Assignee: Hydrate, Inc., Midlothian, VA (US)

( * ) Notice: Subject to any disclaimer, the term of this patent is extended or adjusted under 35 U.S.C. 154(b) by 982 days.

(21) Appl. No.: 11/606,375

(22) Filed: Nov. 30, 2006

(65) Prior Publication Data

US 2007/0137646 A1   Jun. 21, 2007

Related U.S. Application Data

(60) Provisional application No. 60/741,047, filed on Dec. 1, 2005.

(51) Int. Cl.
*A61M 11/00* (2006.01)
(52) U.S. Cl. .......... 128/203.26; 128/204.17; 128/201.13
(58) Field of Classification Search ............. 128/203.12, 128/203.16, 203.17, 203.26, 204.13
See application file for complete search history.

(56) References Cited

U.S. PATENT DOCUMENTS

| | | | |
|---|---|---|---|
| 3,912,795 A * | 10/1975 | Jackson ........................ 261/36.1 |
| 4,086,305 A * | 4/1978 | Dobritz ........................... 261/30 |
| 4,465,067 A | 8/1984 | Koch et al. |
| 4,732,587 A | 3/1988 | Koch |
| 4,844,059 A | 7/1989 | Koch |
| 4,846,783 A | 7/1989 | Koch et al. |
| 5,100,375 A | 3/1992 | Koch |
| 5,242,403 A | 9/1993 | Falb et al. |
| 5,316,542 A | 5/1994 | Koch et al. |
| 5,411,474 A | 5/1995 | Ott et al. |
| 5,443,059 A | 8/1995 | Koch et al. |
| 5,800,335 A | 9/1998 | Koch et al. |
| 5,897,485 A | 4/1999 | Koch |
| 5,935,055 A | 8/1999 | Koch et al. |
| 5,944,651 A | 8/1999 | Koch |
| 6,095,505 A | 8/2000 | Miller |
| 6,102,037 A | 8/2000 | Koch |
| 6,155,255 A * | 12/2000 | Lambert ................. 128/203.16 |
| 6,367,472 B1 | 4/2002 | Koch |
| 6,544,191 B2 | 4/2003 | Koch et al. |
| 6,571,622 B2 | 6/2003 | Koch |
| 6,578,573 B2 | 6/2003 | Koch |
| 6,616,599 B2 | 9/2003 | Koch |
| 6,718,973 B2 | 4/2004 | Koch |
| 6,745,765 B2 | 6/2004 | Kullik et al. |

(Continued)

OTHER PUBLICATIONS

International Search Report and Written Opinion, dated Dec. 5, 2007.

*Primary Examiner* — Steven O Douglas
(74) *Attorney, Agent, or Firm* — McGuire Woods LLP

(57) ABSTRACT

An inline vaporizer disposed in a carrier gas line vaporizes a fluid and adds such vaporized fluid to a carrier gas that flows within the carrier gas line. The vaporizer includes a reservoir or wick that transfers a fluid to a vaporizing element that is adjacent to the reservoir or wick. The vaporizer releases a vapor into the carrier gas line so that the carrier gas flows past the vaporizer to form a vapor and carrier gas mixture.

35 Claims, 17 Drawing Sheets

U.S. PATENT DOCUMENTS

| | | |
|---|---|---|
| 6,926,664 B2 | 8/2005 | Koch |
| 6,951,218 B2 | 10/2005 | Gradon et al. |
| 6,966,693 B2 | 11/2005 | Prakash et al. |
| 6,990,979 B2 | 1/2006 | Koch |
| 6,997,183 B2 | 2/2006 | Koch et al. |
| 7,044,850 B2 | 5/2006 | Koch et al. |
| 7,059,323 B2 | 6/2006 | Kullik et al. |
| 7,066,913 B2 | 6/2006 | Kullik et al. |
| 7,428,902 B2 * | 9/2008 | Du et al. .................. 128/204.17 |

* cited by examiner

INLINE VAPORIZER

CROSS-REFERENCE TO RELATED APPLICATION

This application claims priority under 35 U.S.C. §119(e) to U.S. Provisional Patent Application No. 60/741,047, filed on Dec. 1, 2005, the disclosure of which is expressly incorporated by reference herein in its entirety.

BACKGROUND OF THE INVENTION

1. Field of the Invention

The invention relates to an inline vaporizer, and more particularly to an inline vaporizer disposed within a gas line for mixing a substance such as water into a carrier gas flow.

2. Related Art

Various types of systems have been developed for combining a gas such as air with a vaporized fluid for use in such applications as ventilator humidifiers, drug delivery systems (nebulizer), and combustion apparati creating fuel/gas vaporized mixture (stove burner, fuel injector).

Ventilator humidification systems have been developed to create a mixture of air and water vapor to provide a patient a more comfortable intake of oxygen through the soft tissues of the nose, mouth, and lungs, and to reduce or eliminate damage to the patient's lungs. These systems are an alternative to conventional ventilators and/or humidifiers that provide only dry air, which may damage the respiratory tissues.

As shown in FIG. 1, a conventional ventilator humidifier system 100 may include a ventilator 110, a first feed line 120, a second feed line 125, a water vessel 130, a heater 140, a second heater 145 for the second feed line 125 (such as a heated wire within the second feed line 125), and a return line 150. In the conventional ventilator humidifier system 100, a carrier gas such as air flows from the ventilator 110 through the first feed line 120. The first feed line 120 is connected to the water vessel 130 which contains water. Air in the feed line 120 passes through an open space at the top portion of the water vessel 130 that is not occupied by water.

The water vessel 130 is heated by an adjacent heater 140 to increase the amount of vapor in the water vessel 130. The heater 140 is typically located at the base of the water vessel 130 relatively near the ventilator 110 and outside of the first feed line 120. The heater 140 and the water vessel 130 may be positioned at a distance from the patient. The resulting vapor from the water vessel 130 combines with the air from the first feed line 120 to create a mixture of air and water vapor. The mixture of air and water vapor flows through the second feed line 125 to a patient. Air exhaled by the patient flows through the return line 150 to the ventilator 110.

When providing the mixture of air and water vapor to a patient, some of the water vapor in the second feed line 125 may condense before the mixture reaches the patient. This may occur because the distance between the water vessel 130 and the patient is relatively long and the ambient temperature of the second feed line 125 is generally cool relative to the temperature of the air and water vapor mixture. As a result, the condensed water vapor may collect in the second feed line 125 or return to the water vessel 130 for reheating.

To overcome this problem, a second heater 145 such as a heating coil may be provided within or along the second feed line 125 between the water vessel 130 and the patient. The second heater 145 provides extra heat to increase the temperature of the second feed line 125 and to maintain the water vapor form.

One of the disadvantages of the above-described conventional ventilator humidifier system 100 is that the addition of a second heater 145 along the second feed line 125 requires additional energy, which reduces the energy efficiency of the humidification process. Moreover, the heater 140 has to be turned on for a significant period of time in order to heat up the water in the water vessel 130 before starting air flow. This prolonged start-up time delays the operation of the system 100, and may require a health care provider to expend additional time when treating a patient. In addition, with this configuration, it is difficult to measure or adjust the amount of humidity in the system.

Further, the addition of a heating coil 145 along the second feed line 125 may complicate the operation of the system 100 and render it unwieldy because the bulky heating coil 145 must be positioned near the patient.

The heater 140 also poses a risk of injury, such as burns, because it is positioned outside the first feed line. The external positioning of the heater 140 with respect to the first feed line 120 also results in heat loss to ambient air, which reduces the overall efficiency of the conventional ventilator humidifier system 100.

These and other drawbacks may exist.

SUMMARY OF THE INVENTION

The invention overcomes the disadvantages and drawbacks of the prior art and/or satisfies the need to provide a vaporizer that allows the vaporization of a fluid into a carrier gas stream without having condensation in the stream.

According to one embodiment of the invention, a system for adding a fluid to a carrier gas includes a carrier gas line for directing a carrier gas stream and a vaporizing device located within the carrier gas line. The vaporizing device may include a heating device having an outlet, wherein the fluid is heated to a vapor and is released at the outlet of the heating device. A carrier gas within the carrier gas line flows past the outlet of the heating device to mix and form a vapor and carrier gas mixture. The system may further include a fluid source connected to the heating device that is operable to provide the fluid to the heating device. In addition, the system may further include a carrier gas source coupled with the carrier gas line. For example, the vapor and carrier gas mixture may be delivered to a patient. The system may further include a controller, such that the heating device is responsive to the controller. The controller may include a feedback loop to control power to the heater, such that the power is adjusted faster than the thermal time constant of the heater. The fluid source may also be responsive to the controller. The system may further include a sensor located at a predetermined position along the carrier gas line, such that the controller receives a signal from the sensor. The system may further include a fluid source that is connected to the heating device and is operable to provide the fluid to the heating device, such that the fluid source is responsive to the controller based on a signal from the sensor. The heating device may also be responsive to the controller based on a signal from the sensor. The controller may control at least one of a quantity of fluid delivered to the heating device, a temperature of the heating device, and a flow rate of the carrier gas. The vaporizing device may include a porous material capillarizing the fluid and an orifice disk including at least one orifice proximate the heating device, such that the capillarized fluid passes into the at least one orifice to be vaporized by the heating device. The carrier gas line may include an air hose in fluid communication with a pump at a first end of the carrier gas line and a respiratory interface in fluid communication with the air hose and defining a second end of the carrier gas line.

In another embodiment of the invention, a system for adding a fluid to a carrier gas includes a carrier gas source operative to generate a carrier gas flow, a carrier gas line coupled to the carrier gas source at a first end of the carrier gas line such that the carrier gas line directs carrier gas flow, a fluid source having the fluid disposed therein, and a vaporizer coupled to the fluid source and disposed within the carrier gas line. The vaporizer includes an inlet that receives the fluid from the fluid source a converting element to convert the fluid and an outlet through which the converted fluid enters the carrier gas line to mix with the carrier gas. The system also includes a second end of the carrier gas line downstream from the vaporizer, such that the carrier gas flow includes a mixture of the carrier gas and the converted fluid. The system may further include a controller coupled to the fluid source that is operative to control the concentration of the converted fluid in the carrier gas flow downstream from the vaporizer. The carrier gas line may include an air hose in fluid communication with the pump at the first end of the carrier gas line and a patient respiratory interface in fluid communication with the carrier gas source at the second end of the carrier gas line. The vaporizer may be disposed proximate a connection between the air hose and the respiratory interface. The vaporizer may also disposed proximate a junction between the air hose and the respiratory interface. The respiratory interface may be a mask, for example. The converting element may be a heating element. The vaporizer inlet may include a porous material capillarizing the fluid and an orifice disk including at least one orifice proximate the converting element, such that the capillarized fluid passes into the at least one orifice to be converted by the converting element. The controller may be operative to control at least one characteristic of the mixture of the carrier gas and the vaporized fluid. The controller may include a sensor that senses at least one of a quantity of fluid delivered to the converting element and a temperature of the heating element. The controller controls at least one of the quantity of fluid delivered to the converting element, the temperature of the heating element, and a flow rate of the carrier gas. The converting element may include a nebulizer.

According to yet another embodiment of the invention, a humidifier ventilation system includes a gas source providing a carrier gas flow, a carrier gas line having a first end coupled to the gas source, the air line directing the gas flow, a storage tank storing a liquid include at least water, a vaporizer disposed within the carrier gas line, and a second end of the carrier gas line downstream from the vaporizer, such that the carrier gas flow includes a mixture of carrier gas and the vaporized liquid. The vaporizer includes an inlet in fluid communication with the liquid storage tank, a heating element vaporizing the liquid delivered to the vaporizer via the inlet, and an outlet through which the vaporized liquid mixes with a gas of the carrier gas flow. The carrier gas line may include an air hose in fluid communication with the pump at the first end of the carrier gas line and a respiratory interface in fluid communication with the air hose at the second end of the carrier gas line. The vaporizer may be disposed proximate a connection between the air hose and the respiratory interface. The vaporizer may also be disposed within the respiratory interface. The respiratory interface may be a mask. The vaporizer inlet may include a wick that includes a porous material capillarizing the liquid and an orifice disk including at least one orifice proximate the heating element, such that the capillarized liquid passes through the at least one orifice to be vaporized by the heating element. The system may further include a controller regulating at least one of a rate of the carrier gas flow from the gas source, a quantity of liquid delivered to the vaporizer from the storage tank, and a temperature of the heating element. The controller may include a sensor sensing at least one of the rate of carrier gas flow, the quantity of liquid in the storage tank, and the temperature of the heating element. The controller may include a first input coupled with a first sensor sensing the temperature of the heating element and a second input coupled with a second sensor sensing the rate of the carrier gas flow, such that the controller determines a concentration of vaporized liquid in the carrier gas flow based on the first and second inputs. The carrier gas line may include a holding portion in which at least a portion of the vaporizer is disposed.

In another embodiment of the invention, a system for adding a fluid to a carrier gas includes a vaporizing device that includes a heating device having an outlet such that the fluid is heated to a vapor and is released at the outlet of the heating device. The system also includes a controller such that the heating device is responsive to the controller and a sensor such that the controller receives a signal from the sensor. In addition, the system includes a fluid source connected to the heating device that is operable to provide the fluid to the heating device, such that the fluid source is responsive to the controller based on a signal from the sensor.

Additional features, advantages and embodiments of the invention may be set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention are incorporated in and constitute a part of this specification, illustrate embodiments of the invention and together with the detailed description serve to explain the principles of the invention. No attempt is made to show structural details of the invention in more detail than may be necessary for a fundamental understanding of the invention.

In the drawings.

DETAILED DESCRIPTION OF THE INVENTION

Figure 1:
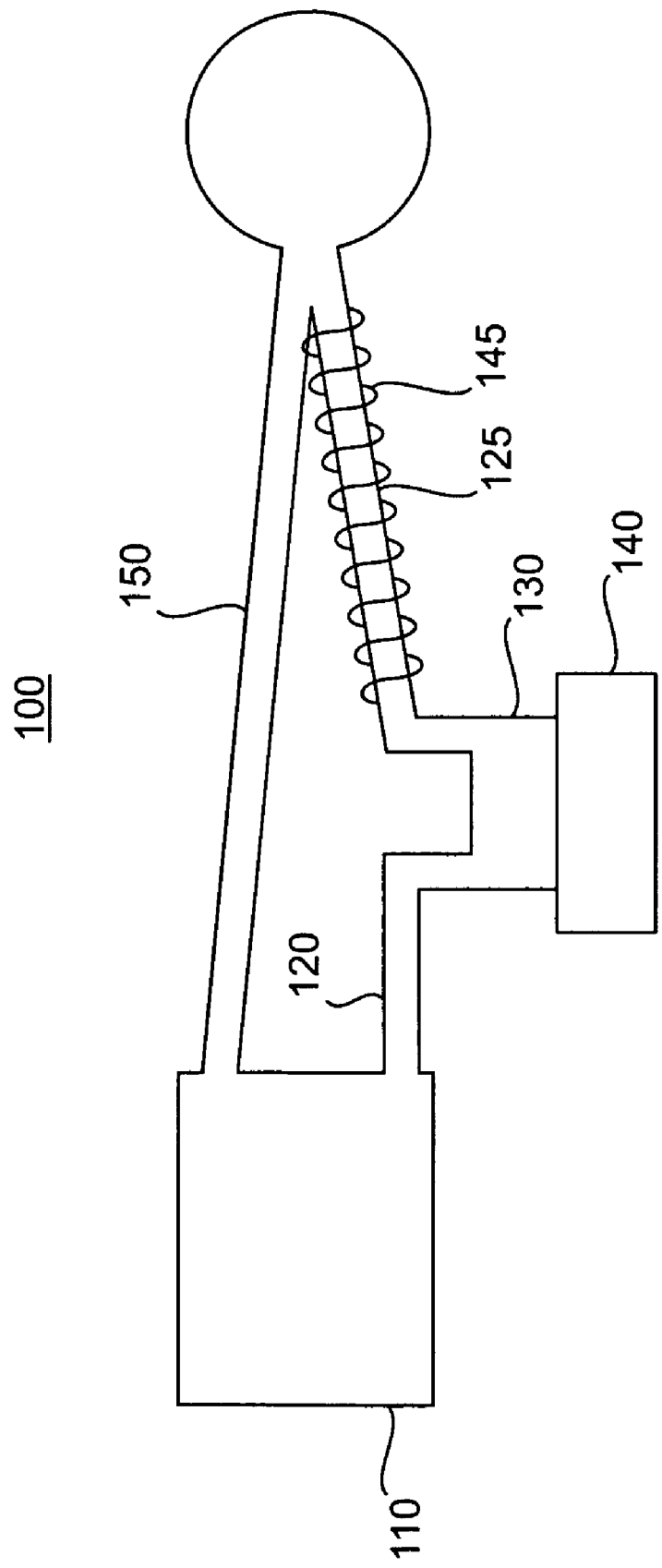
FIG. 1 illustrates a conventional ventilator humidifier.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numbers represent similar parts throughout several views of the drawings. It is understood that the invention is not limited to the particular methodology, protocols, and reagents, etc., described herein, as these may vary. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

For ease of reference, the phrase "carrier gas," as used herein, may be a particular kind of gas or some mixture of gases, such as ambient air. When used to treat a patient, the carrier gas may serve to introduce a vapor into an air passage of the patient, and may also interact with the patient's tissues as well as with a drug or substance being delivered. This interaction may further enhance the chemical or medical activity of the drug or substance, as well as suppress or enhance certain tissue responses to the drug delivered. By way of example, the carrier gas may include, but is not limited to oxygen, nitrogen, helium, nitric oxide, carbon dioxide, or some combination thereof.

A "drug" as used herein, generally refers to a material that can be delivered using the vaporizer of the invention, and may include virtually any medicine, chemical, compound or substance whether in the form of an emulsion, suspension or solution, for vaporization for delivery into the air passage of a patient.

The "drug" to be delivered by the vaporizer of the invention may possess one or more of the following activities which may be used in any combination, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators and xanthines. The active ingredients are commercially available and/or may be prepared by techniques known in the art. According to an embodiment of the invention, the active ingredient may be formulated as a fluid solution, suspension, aerosol propellant or dry powder loaded into a suitable dispenser for administration, such as the nebulizer of the invention. Furthermore, the active ingredient of the invention may be used in combination with at least one pharmaceutically acceptable carrier or excipient. Acceptable carriers or excipients are non-toxic, aid administration and do no adversely affect the therapeutic benefit of the compound. Specifically, for example, the excipient may be a gaseous excipient that is generally available to one of skill in the art.

In addition, "patient," as described herein, includes humans or animals that require, due to a disease state, a treatment regimen, or desired delivery of an effective dose of a drug or humidified air via inhalation.

Figure 2:
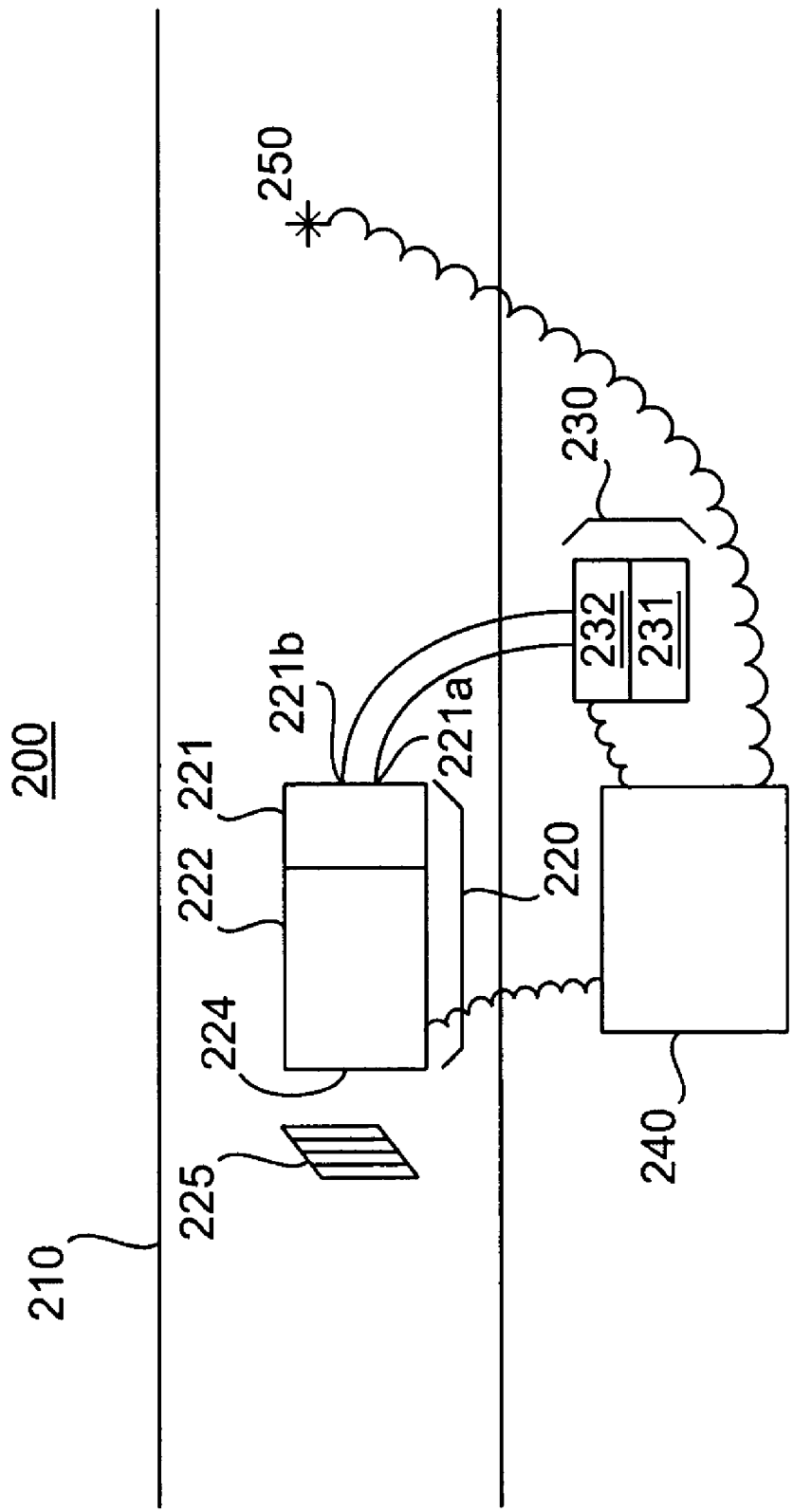
FIG. 2 illustrates an inline vaporizer disposed in a carrier gas line according to principles of the invention.

FIG. 2 illustrates an inline vaporizer system 200 including a carrier gas line 210 and a vaporizer 220 according to principles of the invention. A carrier gas flows from a carrier gas source, such as a ventilator, a pressurized gas source, or a gas cylinder (not shown), through the carrier gas line 210. The vaporizer 220 is located within the carrier gas line 210 and includes a reservoir 221 that holds a fluid and a vaporizing element 222 that is coupled with the reservoir 221. According to an embodiment of the invention, the reservoir 221 may include a material, such as a wicking material, that assists in transferring the fluid to the vaporizing element 222. The reservoir may also include a fluid inlet 221a. According to an embodiment of the invention, the outlet 224 of the vaporizer 220 may be oriented toward the carrier gas source. This orientation of the vaporizer 220 may provide for good mixing between vapor that is released from the outlet 224 and the carrier gas. Alternatively, the vaporizer 220 may be positioned such that the outlet 224 is oriented away from the carrier gas source.

Although the outlet 224 is shown along a center axis of vaporizer 220, it is understood that vapor also may be emitted at the edges. A baffle 225 may be positioned adjacent to the outlet 224 or in another suitable position in the carrier gas line 210 to create turbulence in vapor that is released from the outlet 224 and the carrier gas. The baffle 225 also ensures that the air stream is not directed at the heater surface, which could hinder accurate temperature control.

The inline vaporizer system 200 further includes a fluid source 230 that provides fluid to the reservoir 221. The fluid source 230 is in fluid communication with the fluid inlet 221a of the reservoir 221. In addition, a controller 240 may be coupled to the fluid source 230, the vaporizer 220, and a sensor system 250 that is located in the carrier gas line 210.

The reservoir 221 holds a fluid, such as water, and/or a drug, for example. The fluid from source 230 may enter the reservoir 221 through the inlet 221a. In order to prevent an excessive amount of fluid from collecting in the reservoir 221, the fluid source 230 may include a fluid container 231 and a pump 232 to provide a fluid from the fluid container 231. The pump 232 may be a positive pressure pump or a positive displacement pump. Other feed processes, such as capillary action and/or gravity feed may also be used. Alternatively, the reservoir 221 may include a fluid outlet 221b that removes fluid and cycles it back to the container 231 to prevent an accumulation of fluid in the reservoir 221. Reservoir 221 may be of any size, and in one embodiment of the invention, no reservoir 221 is used.

A portion of the fluid moves from the reservoir 221 to the vaporizing element 222. The fluid is then vaporized by vaporizing element 222 and is released from the outlet 224 as a vapor. This vapor combines with the carrier gas in line 210 to form a vapor and carrier gas mixture that may be supplied to a desired location, such as a patient using a respiratory interface at a terminal end of the carrier gas line 210.

The vaporizing element 222 may be a heater that heats the fluid to vapor. However, it is understood that other devices, such as a nebulizer and/or a pressurized vaporizer may also be used as the vaporizing element 222, e.g., convert fluid to add it to a carrier gas, or may be used in connection with a heater to introduce a liquid into a carrier gas. Moreover, fluid from the reservoir 221 may travel to the vaporizing element 222 through any type of connection. For example, the fluid may be drawn from the reservoir 221 through a controller (not shown) via capillary action to the vaporizing element 222, as described later with reference to FIGS. 11A and 11B. According to an embodiment of the invention, the heater and reservoir described above may include the devices described in U.S. Pat. No. 6,634,864, U.S. Patent Application Publication No. US 2004/0151598 (application Ser. No. 10/691,067), and U.S. Provisional Patent Application No. 60/741,646, filed Dec. 1, 2005, and PCT Application No. PCT/US06/46030 (WIPO Publication No. WO 2007/064909), filed Nov. 30, 2006, titled "Advanced Capillary Force Vaporizer," the contents of which are incorporated herein by reference in their entirety.

The inline vaporizer system 200 may further include a controller 240 that communicates with the vaporizer 220. In addition, the controller 240 may communicate with the fluid source 230. A sensor system 250 may be positioned at a predetermined position along the carrier gas line 210. According to an embodiment of the invention, the sensor system 250 may be positioned at a location near the recipient of the carrier gas and vapor mixture such that the sensor system 250 sends a signal to the controller 240. The signal sent by the sensor system 250 to the controller 240 may include data regarding temperature, flow rate, and/or vapor content of the vapor and carrier gas mixture, for example. The sensor system 250 may include individual sensors at one or more locations that detect temperature, flow rate, and/or vapor content data. The controller 240 processes the signal from the sensor system 250 and communicates with the vaporizing element 222 and the fluid source 230 accordingly.

According to an embodiment of the invention, the controller 240 may adjust the rate of vaporization at the vaporizing element 222 by controlling various functions. For example, the controller 240 may regulate the flow of carrier gas from the carrier gas source. The controller 240 may also control the pump 232 to adjust the amount of fluid that flows from the fluid container 231 to the inlet 221a of the reservoir 221. In addition, if the vaporizing element 222 is a heater, the controller 240 may control the temperature of the heater to maintain a suitable rate of vaporization. Since the controller 240 can regulate the flow of carrier gas and vapor, the vapor content in the water vapor and carrier gas mixture may be calculated easily. The controller 240 will be described in greater detail below in reference to FIG. 6.

Figure 3:
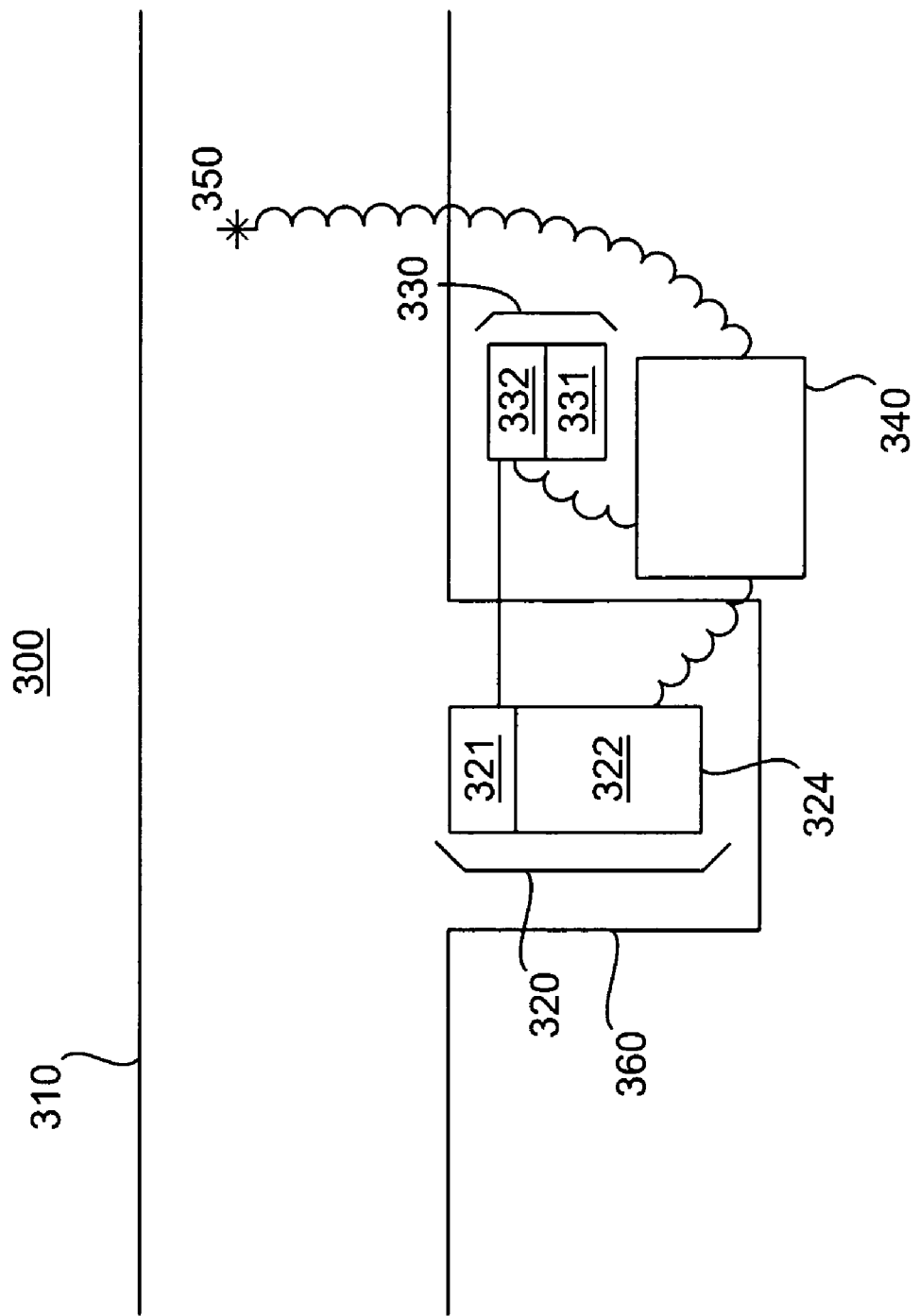
FIG. 3 illustrates an inline vaporizer disposed in a carrier gas line at an offset position according to principles of the invention.

FIG. 3 illustrates an inline vaporizer disposed in a carrier gas line at an offset position according to principles of the invention. The system 300 includes a vaporizer 320 that is positioned within a holding portion 360 of a carrier gas line 310 where the vaporizer 320 is offset from the carrier gas stream. The vaporizer 320 may include a reservoir 321 and a vaporizing element 322. In this embodiment, a carrier gas flows from a source (not shown) through the carrier gas line 310 in a stream. The vaporizer 320 is positioned in the holding portion 360 which is recessed in the carrier gas line 310. The vapor that is generated in the vaporizer 320 mixes into the stream to form a carrier gas and vapor mixture.

In FIG. 3, the vaporizer 320 is shown to be positioned completely within the holding portion 360 with the outlet 324 pointed away from the carrier gas stream but the invention is not limited thereto. For example, the vaporizer 320 may be positioned partially in the holding portion 360 and partially in the carrier gas stream. The holding portion 360 may be positioned at an angle of about 90° relative to the carrier gas line 310. However, the holding portion 360 may be recessed at any angle relative to the carrier gas line 310.

Figure 4:
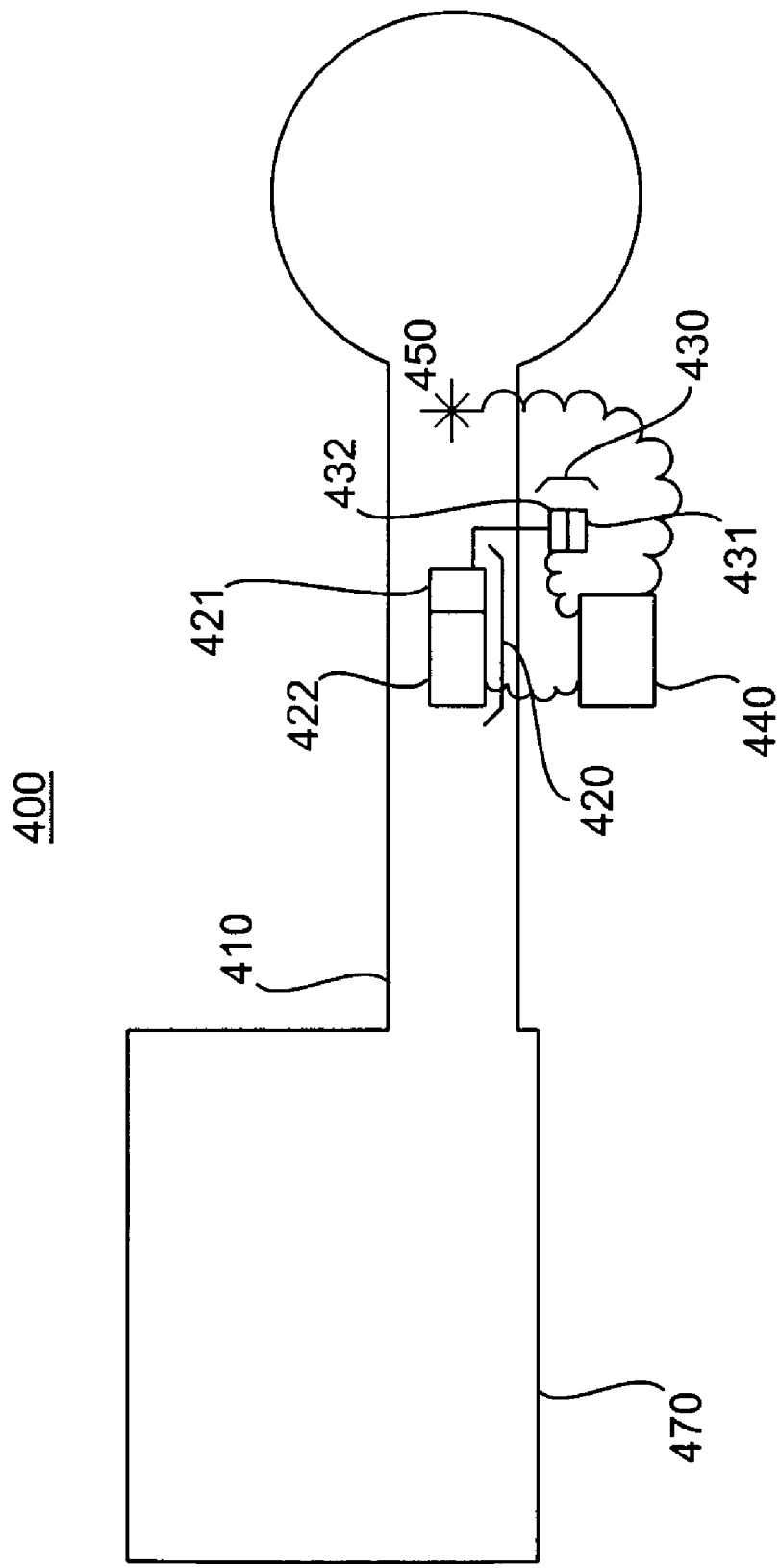
FIG. 4 illustrates an inline vaporizer system including a carrier gas line, a vaporizer disposed therein, and a carrier gas source according to principles of the invention.

In another embodiment of the invention as illustrated in FIG. 4, the inline vaporizer system 400 may include a carrier gas source 470 connected to a carrier gas line 410 and a vaporizer 420, which may include a reservoir 421 and a vaporizing element 422. For example, the inline vaporizer system 400 may be used as a humidified ventilator system that provides humidified air, for example, to a patient or to a neonatal patient in an incubator. The carrier gas line 410 that contains the vapor and carrier gas mixture may be provided directly to a patient. The carrier gas line 410 and vaporizer 420 may be disposable to ensure that the system 400 is sterile and suitable for use with patients. In one example, the carrier gas source 470 may be a ventilator, the carrier gas may be air, and the fluid stored in a reservoir 421 may be water such as distilled water. Alternatively, the carrier gas source 470 may be an air compressor or a gas cylinder that provides air as the carrier gas. According to an embodiment of the invention, the carrier gas may be heliox. Although no return line is shown in FIG. 4, it is understood that such a return line may be used.

The vaporizer 420 may be positioned at a location that is sufficiently close to the patient to substantially avoid condensation in the carrier gas line 410 between the vaporizer 420 and the patient. For example, the vaporizer 420 may be located at a position about 6-18 inches from the patient. Alternatively, the vaporizer 420 may be closer to the patient, or even within a patient, such as if a very small vaporizer is located within a bronchoscope.

The inline vaporizer system 400 provides a vapor and carrier gas mixture while reducing or eliminating condensation formed in the line, without using an additional heat source and/or insulation along the carrier gas line to prevent such condensation. Thus, the inline vaporizer system of the invention may be more energy efficient than conventional systems.

The invention provides a heating device within the carrier gas line thereby improving the efficiency of the system since substantially all the heat is transferred to the fluid and the carrier gas. In addition, the risk of a user, such as a health care provider, burning themselves is greatly reduced or eliminated as the heater is not exposed while the heater is in use but is enclosed within the carrier gas line.

The inline vaporizer system 400 may also include a drug delivery system 430 in which a drug is provided to the reservoir 421 and is vaporized and mixed with the carrier gas from the carrier gas source 470 and is provided to a patient. The drug delivery system 430 may include a fluid source 431 and a pump 432. For example, the fluid source 431 may be used to supply the drug from the drug delivery system 430 at a specific dosage that is suitable for a patient. The drug may also be injected into a line that feeds fluid from the fluid source 431 to the reservoir 421 via the pump 432. For drug delivery, it may be preferable that the reservoir 421 not include an outlet so that the entire amount of the drug is supplied to the patient and none is cycled back to the fluid source 431 as waste. Thus, the inline vaporizer system 400 may be operated until the controller 440 determines that the entire dosage of the drug has been administered. Alternatively, a pre-vaporized drug may be added to the carrier gas line 410 such that it is mixed with the carrier gas before the vaporizer 420 mixes the fluid and the carrier gas.

According to another embodiment of the invention, a separate nebulizer or aerosolizer (not shown) may be placed in the feed line to introduce the drug into the carrier gas stream. The nebulizer or aerosolizer may introduce the drug while the vaporizer 420 of the invention is operating to introduce the liquid to the carrier gas stream. Alternatively, the vaporizer 420 may be turned off while the nebulizer or aerosolizer is turned on to introduce the drug into the carrier gas stream. This may increase the concentration of drug available to a patient.

Further, controller 440 may include an alarm to alert a health care provider that the fluid source 431 and/or the reservoir 421 have been emptied and/or that the drug has been fully vaporized and administered to the patient via the carrier gas line 410. For example, the alarm may sound in response to a signal from the sensor system 450 indicating that the amount of drug detected in the vapor and carrier gas mixture is below a certain threshold or if the power supplied to the heater is less than what it should be for the set pump rate. Such an alarm would allow the health care provider to terminate use of the inline vaporizer system 400. Alternatively, the controller 440 may operate on a timer and have an automatic shut-off that can either turn off the inline vaporizer system 400 or cause the alarm to alert a health care provider when the drug has been fully provided.

The inline vaporizer system 400 may be used in other environments, such as a fuel injector for a combustion apparatus in which fuel stored in the reservoir 421 is vaporized and mixed with a carrier gas from the carrier gas source 470. However, the applications of the inline vaporizer system 400 are not limited to the embodiments listed here as other uses will be recognized by one of ordinary skill in the art.

Figure 5:
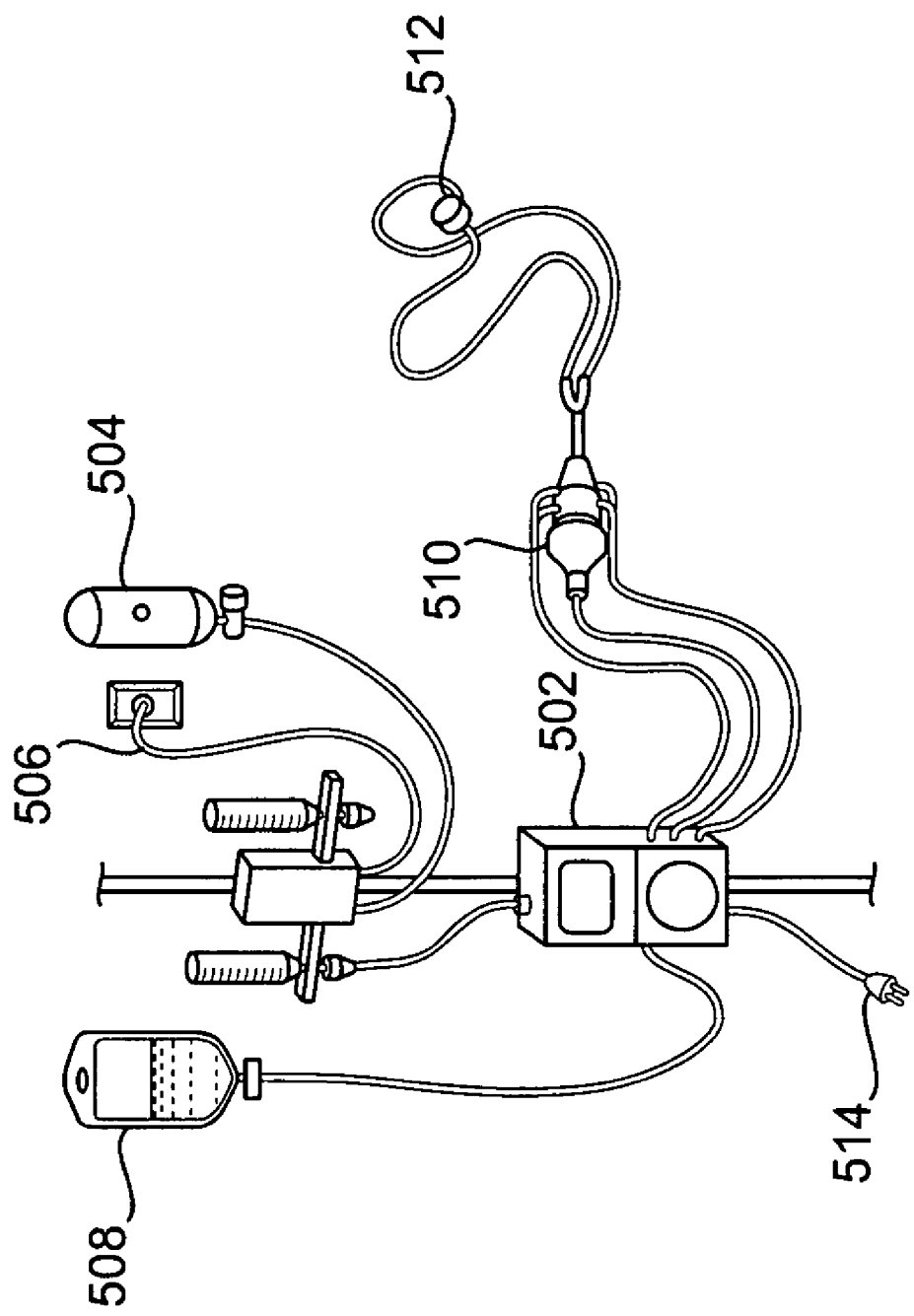
FIG. 5 illustrates a high flow carrier gas system according to principles of the invention.

FIG. 5 illustrates a high flow carrier gas system 500 according to principles of the invention. The high flow carrier gas system in FIG. 5 is an embodiment of a system in which humidified carrier gas is provided to a patient. The system includes a controller 502, a gas supply 504, a dry air supply 506, a fluid supply 508, a heater device 510, a connection to a patient 512, and a power supply 514.

The carrier gas may include, but is not limited to air and heliox. The fluid supply 508 may be a container such as a sterile bag holding water. Due to the presence of a pump in the controller 502, the bag 508 may be positioned at any location with respect to the controller 502. In addition, the amount of water in the bag 508 may be measured by a weight gauge (not shown) or a volume gauge positioned near the bag or in the controller. An operator may provide a specific mass or volume of water to a patient. When the mass or volume of water reaches a specified critical level, an alarm may alert a user of such conditions.

In one embodiment of the invention, a differential pressure sensor is located in the heater device 510 or the controller 502 and is used in combination with the controller 502 to ensure that adequate humidified carrier gas is being supplied to a patient. The differential pressure sensor is calibrated to detect the carrier gas flows in the system 500 thus accurately providing the desired amount of gas at the desired conditions. A differential pressure sensor used in the invention may be any conventional differential pressure sensor known in the art, such as MPXHZ6250A or MPXHZ6400A offered by Freescale®. Based on the readings from the pressure sensor, the controller 502 may increase, decrease, or maintain the flow rate of the carrier gas and/or the fluid. Altering the flow rate of the carrier gas also allows some control of the temperature and humidity in the system 500. For example, the temperature of the carrier gas can be increased without increasing the humidity in the system 500 by decreasing the flow rate of a relatively cooler carrier gas. In addition, altering the flow rate of the fluid can allow control of the temperature of the mixture in the carrier gas. For example, the carrier gas temperature can be increased by increasing the fluid flow rate, as well as by decreasing the gas flow rate or increasing the heater temperature. Other methods of measuring fluid flow besides using a differential pressure sensor may also be used.

As discussed earlier, the controller 502 may be used to control power to the heater device 510. In one embodiment of the invention, this control may be achieved using a feedback loop that provides feedback control faster than the thermal time constant of the heater device 510 used without a humidification system. This allows the heater device 510 to be controlled and adjusted faster than the heater device 510 temperature increases, thereby avoiding overheating and damaging the heating element.

Figure 6:
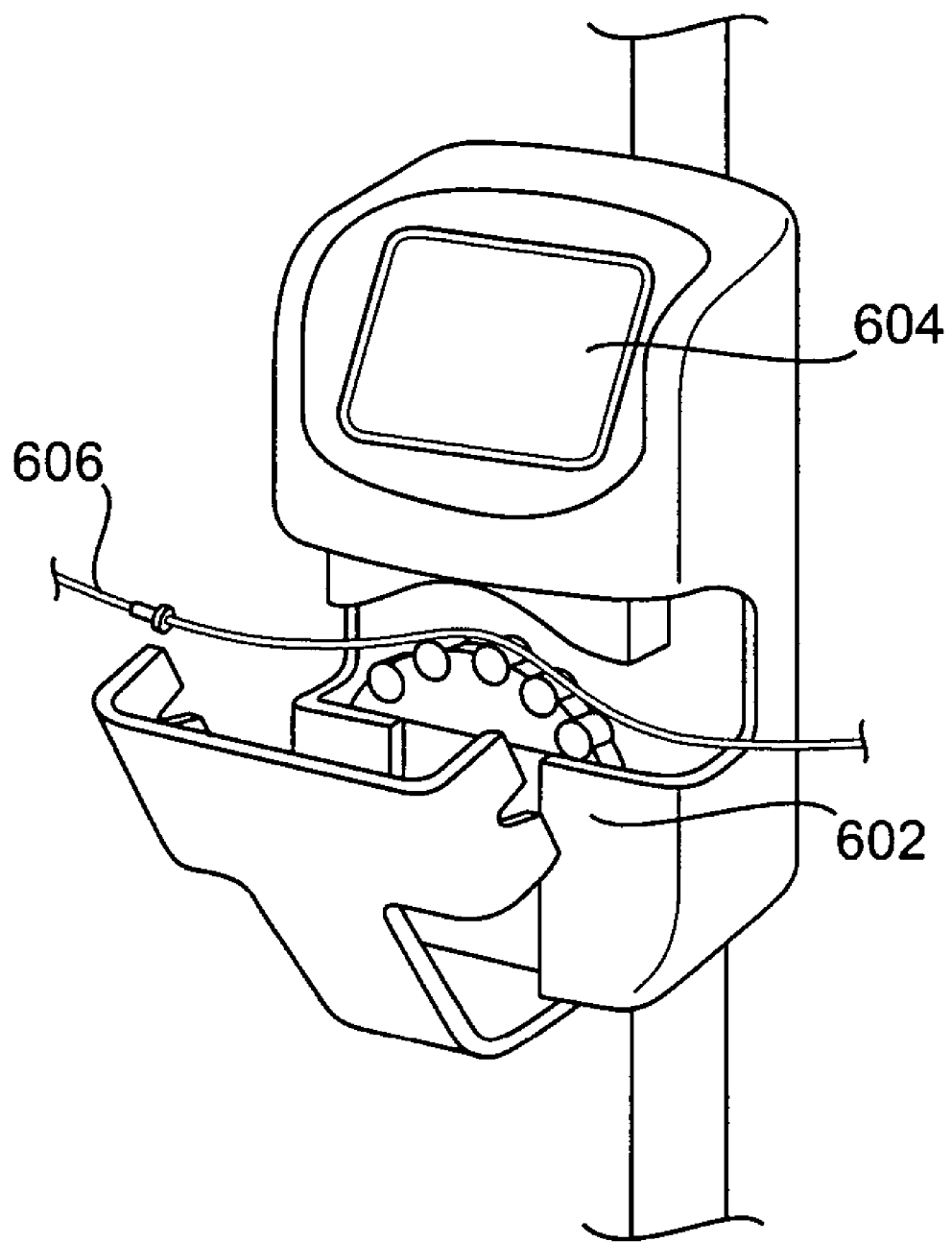
FIG. 6 illustrates a controller with a pump wheel and display according to principles of the invention.

The controller 502 in FIG. 5 may be any suitable controller, such as that shown in FIG. 6. FIG. 6 illustrates the controller 502 that includes a pump wheel 602 and a display 604. As shown in FIG. 6, the pump wheel 602 pumps fluid in tubing 606 towards the heater device 510. In this embodiment, the pump wheel 602 is positioned below the display 604 so that any possible fluid leaks do not contact the electronics of the display 604.

Figure 7:
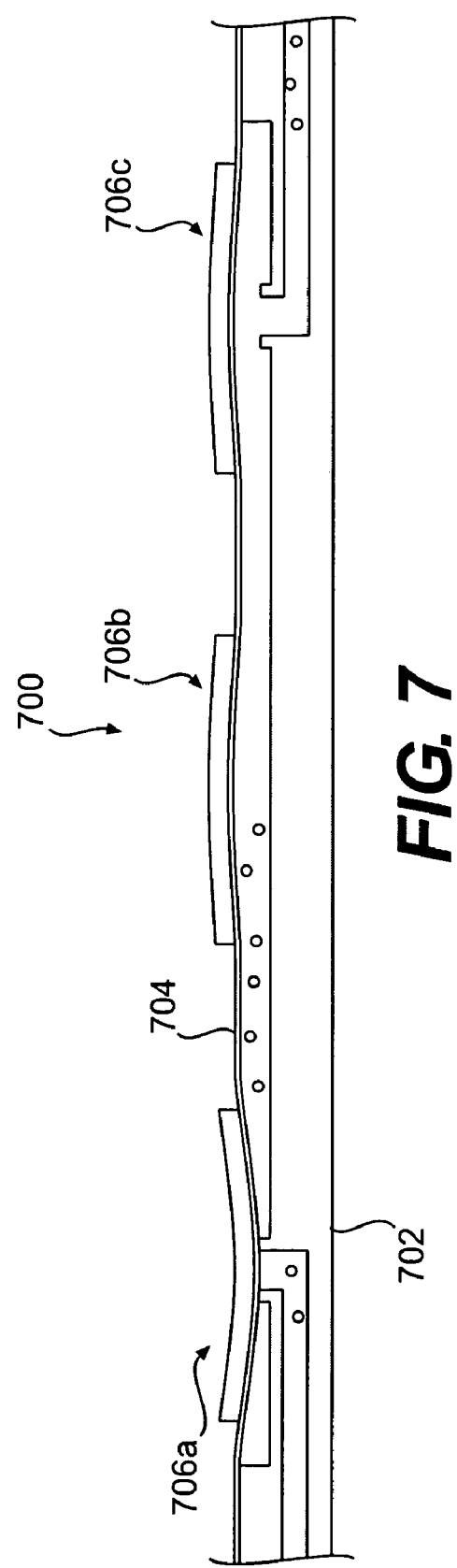
FIG. 7 is a schematic diagram of a micropump that may be used with a controller according to principles of the invention.

In another embodiment of the invention, the controller 502 may use a micropump to move fluid towards the heater 510 instead of using a pump wheel 602. Alternatively, a micropump may be positioned at the bag 508 to pump fluid directly from the bag 508. Any type of micropump may be used, and preferably one that is inexpensive and can be replaced frequently. For example, as illustrated in FIG. 7, a micropump 700 may utilize a plastic body 702, a metal diaphragm 704, and three piezo PZT ceramics, 706a, 706b, and 706c. The PZT ceramics 706a, 706b, and 706c are glued onto metal diaphragm 704 to form two active valves (an inlet and an outlet) and one actuation diaphragm. The valve seats, the pump chamber, and the inlet/outlet interfacing channels are formed in the plastic body 702. For example, the plastic body 702 may be made of polyetheretherketone (PEEK) and the metal diaphragm may be made of stainless steel.

Upon actuation of a voltage, each of the three PZT ceramics may be controlled independently. The micropump is able to pump bidirectionally and may pump both gases and liquids. For example, each actuation unit may perform a stroke of more than 40 µm. Additional details on the operation of an example of such a micropump are provided in PCT/EP03/09352, filed Aug. 22, 2003, titled "Peristaltic Micropump," the disclosure of which is incorporated by reference herein in its entirety. In addition, other types of micropumps may be used.

Figure 8:
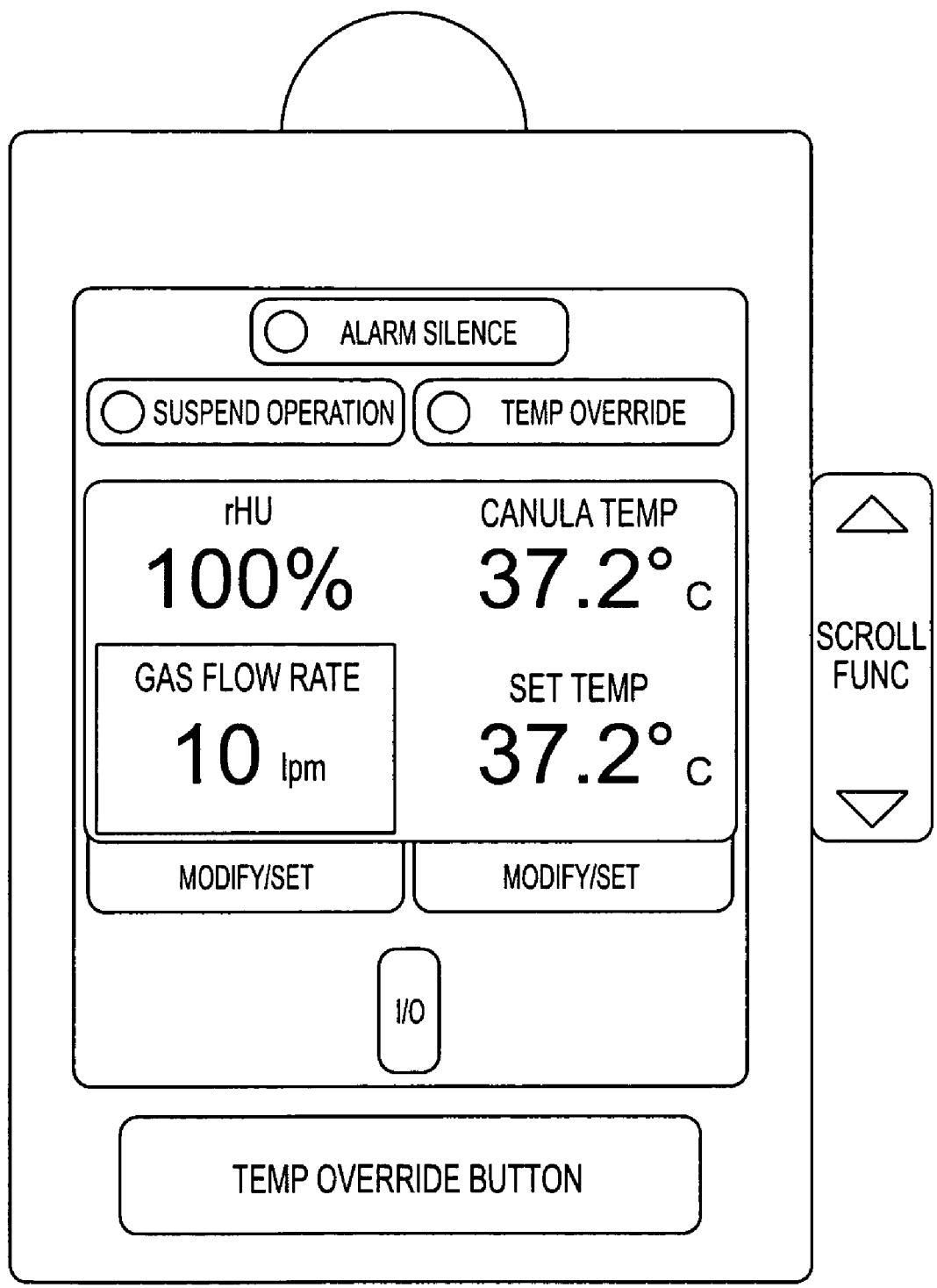
FIG. 8 illustrates a display of a controller illustrated in FIG. 6.

Referring back to FIG. 6, the display 604 may be an LCD display, for example, as shown in FIG. 8. According to an embodiment of the invention, the display 604 may display information including, but not limited to relative humidity (rHU), absolute humidity, gas outflow temperature (shown in FIG. 8 as cannula temperature), gas flow rate, fluid flow rate, and set temperature. In addition, the display 604 may include touch controls to turn the controller 502 on or off, silence an alarm, suspend operation, or to override a set temperature, for example. The display 604 may also include touch controls to modify set temperatures or flow rates and to scroll to various display options. Further, in one embodiment of the invention, an additional remote display may be added so that it can be controlled at a short distance from the system 500, such as from across a room.

In addition, the controller 510 may include an alarm that meets various standards and regulatory requirements, such as IEC 60601-1-8 requirements, for example. This type of alarm would allow alert a user of any problems with the system such as if the gas supply 504 or the fluid supply 508 is running low.

Figure 9:
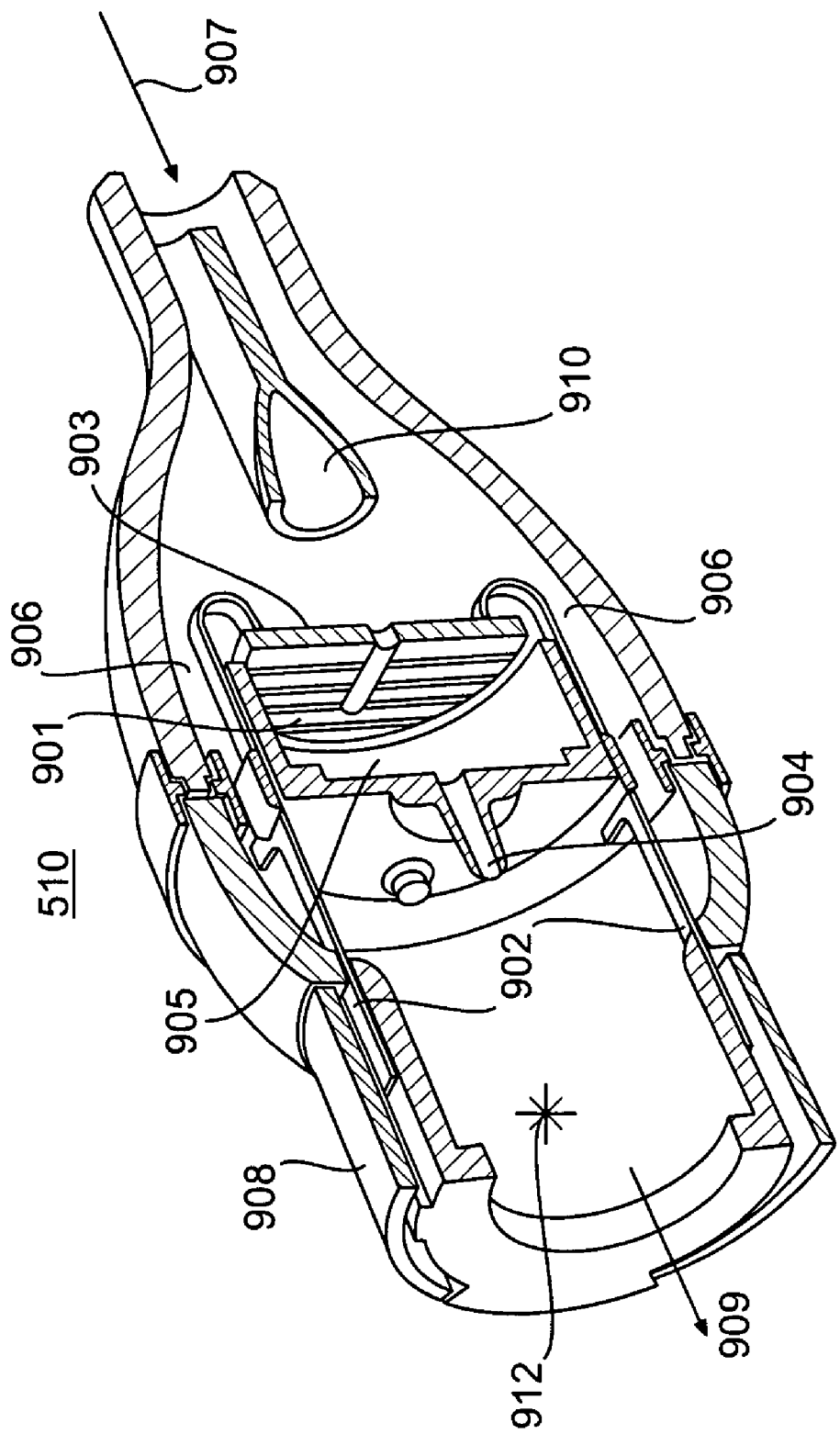
FIG. 9 is a cut away view of a heater device of the system illustrated in FIG. 5.

FIG. 9 is a cut away view of the heater device 510 of the system illustrated in FIG. 5. The heater device 510 may include a heater housing 901 including electrical leads 902 and a heating element 903, a fluid inlet 904, a reservoir area 905, gas passages 906, a carrier gas inlet 907, a connector 908, a humidified gas outlet 909, and a baffle 910.

The electrical leads 902 may be connected to a controller to regulate the temperature of the heating element 903. The fluid inlet 904 may be coupled with a fluid source to provide a fluid, such as water, to the reservoir area 905. The reservoir area 905 may include a porous material (not shown) such that the fluid is provided to the heating element 903 through capillary action.

The heating element 903 may be electrically coupled to a switch (not shown) such as a field effect transistor (FET) switch, for example. A safety relay may be added in series with the heating element 903 and FET switch circuit. If the FET switch is on for too long, depending on the control timing, e.g. more than five (5) milliseconds, the relay opens and shuts down power to the heater preventing overheating.

The connector 908 couples the electrical connections between the connection to the patient 512 shown in FIG. 5 and the heater device 510 to prevent accidental disconnection and to avoid contamination of the connections to maintain sterile use. The connector 908 may be formed such that the heater device 510 may be disconnected from the patient 512 while the electrical connections remain coupled.

To avoid overheating or cracking the heater device 510, a start-up sequence may be used that allows the ramping up of the temperature. For example, the temperature may be ramped up at about 1° C. every 3.5 milliseconds (ms), or a total of 100° C. in 350 ms.

The heater device 510 may further include a sensor 912 such as a C4 sensor, for example, that detects the conditions in the heater device 510. The sensor 912 may be positioned inside the heater device 510 near the humidified gas outlet 909.

Figure 10:
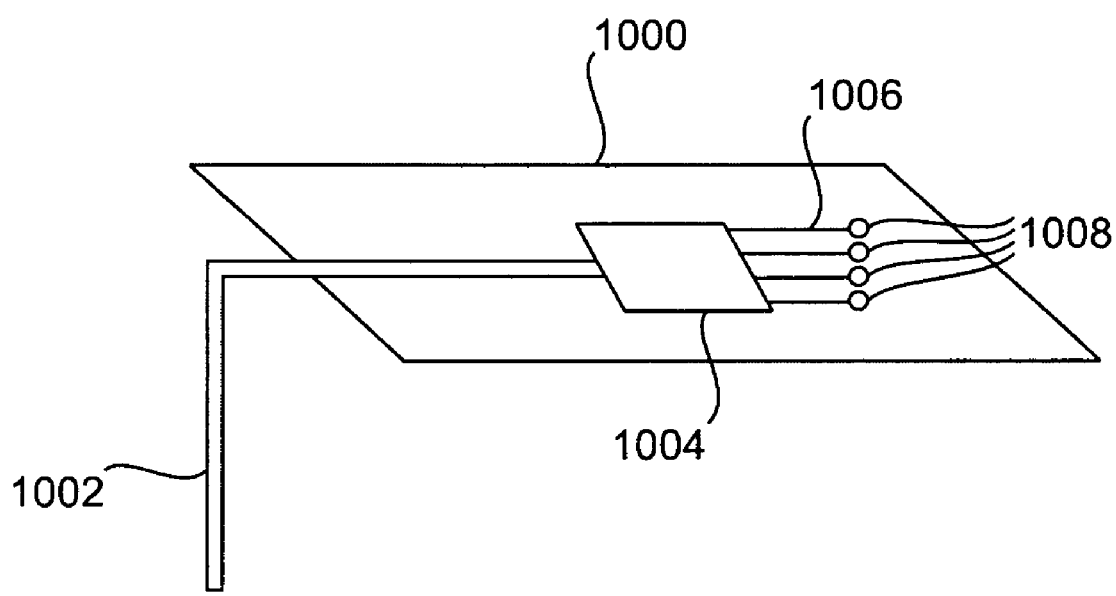
FIG. 10 illustrates a memory device that is coupled with a controller.

In particular, the sensor 912 may include a memory device assembly 1000, as shown in FIG. 10 that is coupled with the controller 502. The memory device assembly 1000 may include a fin 1002 made of a thermally conductive material such as copper, for example, that aids the sensor 1012 in detecting gas temperature and thus allows the sensor 1012 to measure the temperature in the heater device 510. The memory device assembly 1000 also includes a temperature circuit 1004 on the memory device assembly 1000 that is connected to the fin 1002. Circuit 1004 may include various components, such as a processor, memory, digital to analog converter, and/or other components. Leads 1006 may connect circuit 1004 to contacts 1008. One or more wires may connect contacts 1008 to the heater device 510 via connector 908 shown in FIG. 9, thereby connecting the circuit 1004 to the heater device 510.

With the information provided by the memory device assembly 1000, the heater device 510 may also be controlled manually by overriding the automatic feedback settings. The memory device assembly 1000 may further be used to store calibration data for the heater device 510 and a pump, if necessary. In addition, the memory device assembly 1000 may be used to monitor the usage of the heater device 510. For example, the memory device assembly 1000 may be programmed to limit the usage of the heater device 510 to a defined length of time based the heater device's lifespan and to avoid clogging of the heater device 510 with condensation. For example, the memory device assembly 1000 may be set to allow use of the heater for fourteen days, where the heater may be used only during the fourteen days after the device is first used. Alternatively, the device may calculate and track the actual time in use, and only allow a total time of usage of fourteen days, for example. In addition, the memory device assembly 1000 may provide details on its own identifying information. Other types of sensors and memory devices may also be used.

Figure 11A:
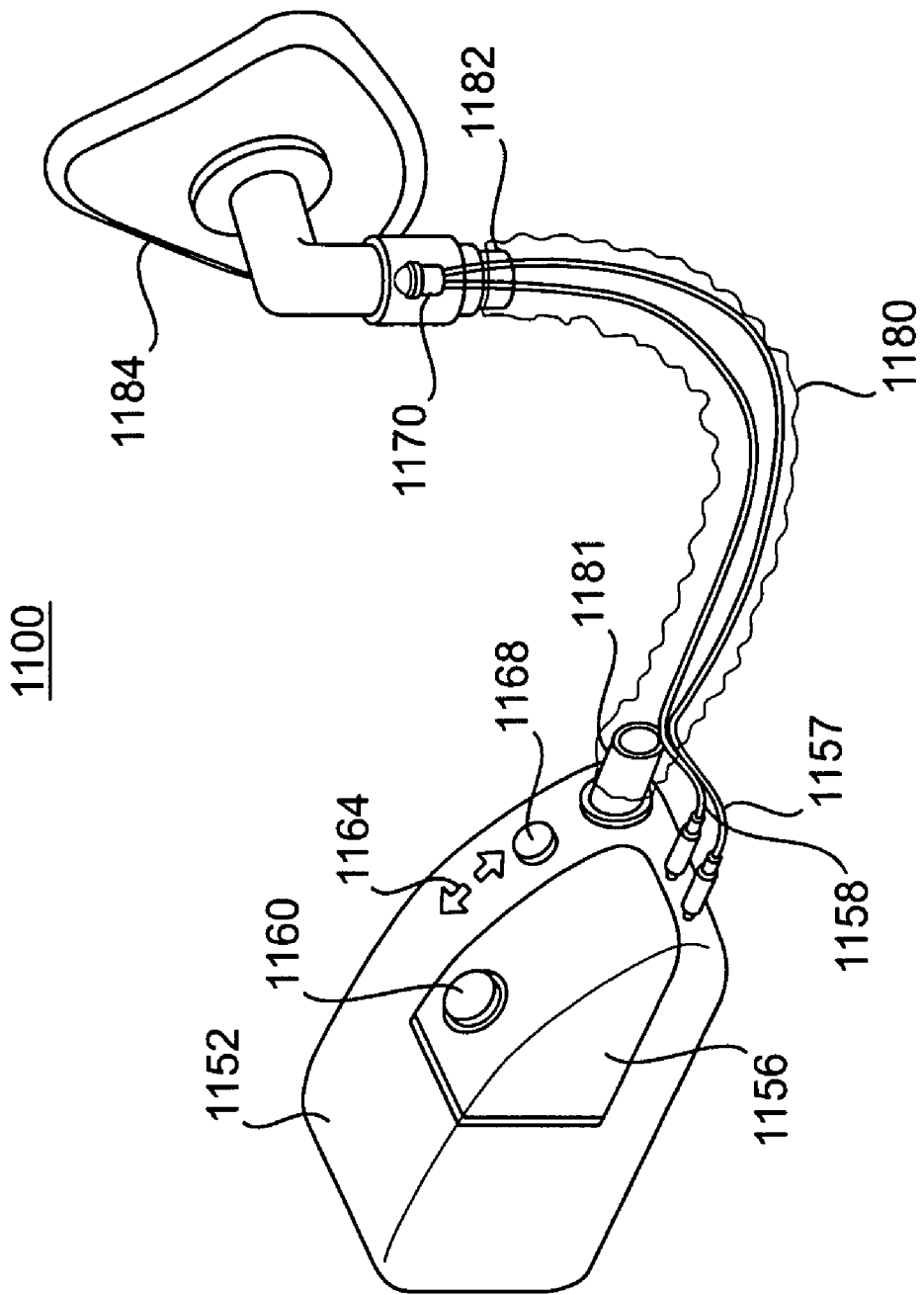
FIG. 11A illustrates a non-invasive humidifier system having a vaporizer disposed proximate a patient respiratory interface according to principles of the invention.

FIG. 11A illustrates a non-invasive humidifier 1100 having a vaporizer disposed proximate a respiratory interface according to principles of the invention. The humidifier 1100 may be used to provide a patient with humidified air, for example. The humidifier 1100 includes a gas source such as a pump 1152 that provides continuous positive airway pressure (CPAP) along a carrier gas line 1180 towards the respiratory interface 1184. The respiratory interface may include, but is not limited to a mask, mouthpiece, nasal cannula, endotracheal tube, and a patient "Y." The pump 1152 is controlled based on the speed of the blower that provides air to the respiratory interface 1184. Any gas source may be used for pump 1152, such as, for example, a blower that blows ambient air or a pressurized gas tank, which may provide a gas flow from a first end 1181 of the gas line towards a second end 1182 of the gas line proximate the respiratory interface 1184.

Disposed within the respiratory interface 1184 is the vaporizer 1170. The humidifier also includes a liquid storage tank 1156 holding a fluid, like water, that is fluidly connected to the vaporizer 1170 via a fluid feed line 1158. Flow rates of about 250 µL/s to about 300 µL/s may be achieved using a fluid reservoir. Fluid flow rates of about 2.2 mL/min (0.036 mL/sec) may be set to provide 100% relative humidity using 50 liters per minute (Lpm) (833 mL/sec) of continuous flow of dry air at 37° C. The fluid flow capacity is based on size of heater/ceramic and power supply. For example, a heater with a diameter of 19 mm and a power supply of 100 W may be used to achieve the level of flow described above. Smaller or larger heaters with higher or lower power supplies may also be used.

The liquid storage tank 1156 may include an opening 1160 to refill the liquid. According to an embodiment of the invention, the storage tank 1156 does not have to be within the same housing as the pump or gas source 1152. The vaporizer 1170 may receive power over an electrical line 1157 coupled to the pump 1152.

Figure 11B:
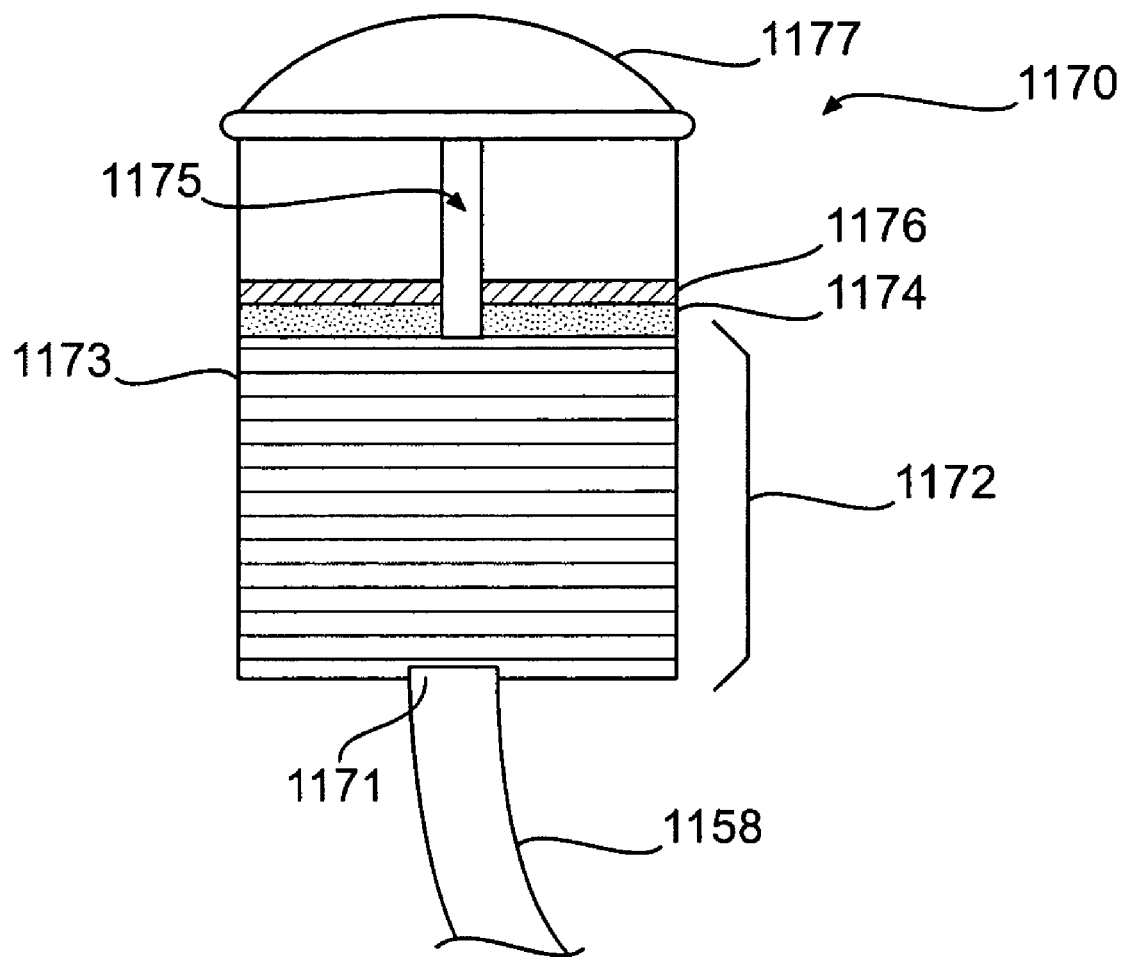
FIG. 11B is a cross-sectional view of the vaporizer from the humidifier system illustrated in FIG. 11A.

FIG. 11B is a cross-sectional view of the vaporizer 1170 from the non-invasive humidifier 1100 illustrated in FIG. 11A. According to an embodiment of the invention, the vaporizer 1170 may be a capillary force vaporizer (CFV). The vaporizer 1170 may be approximately the size of the dime and is highly energy efficient. The vaporizer 1170 includes an inlet 1171 that includes a wick 1172 located in a reservoir portion having one or more layers 1173 of a porous material that capillarize the liquid drawn from the feed line 1158. The capillarized liquid becomes a vapor and exits through an orifice disk 1174 that may have one or more orifices 1175, but a single orifice is preferred. The capillarized vapor can then be heated by the heating element 1176 and exit through outlet 1177.

When using a CFV, start-up and shut-down sequences may be performed to ensure safe and proper operation of the CFV. In one example of such a sequence, before beginning operation of a CFV, air flow across the CFV is initiated. The unit is then powered on to reach a set temperature. Then, the flow of water is initiated to prime the lines. When vaporizing the water, the pump rate of the water is set to correlate with the air flow and the set temperature. After sufficient vaporization is achieved, similar steps including turning off fluid flow and stopping power supply to the vaporizer 1170 may be taken to shut down the CFV.

The vaporized liquid mixes with the gas flow provided by gas source 1152 to humidify the air within respiratory interface 1184. Providing humidification at the respiratory interface 1184, which is a mask in this example, greatly reduces the "rain-out" effect that can cause the carrier gas line 1180 to become dirty and filled or clogged due to excess moisture, thus restricting gas flow. The ventilator humidifier 1100 may be manually controlled using, for example, temperature 1164 and power 1168 controls. The ventilator humidifier 1100 may also be controlled automatically by implementing a controller that can adjust humidification based on feedback provided by a sensor system such as the system illustrated in FIG. 2.

Figure 12:
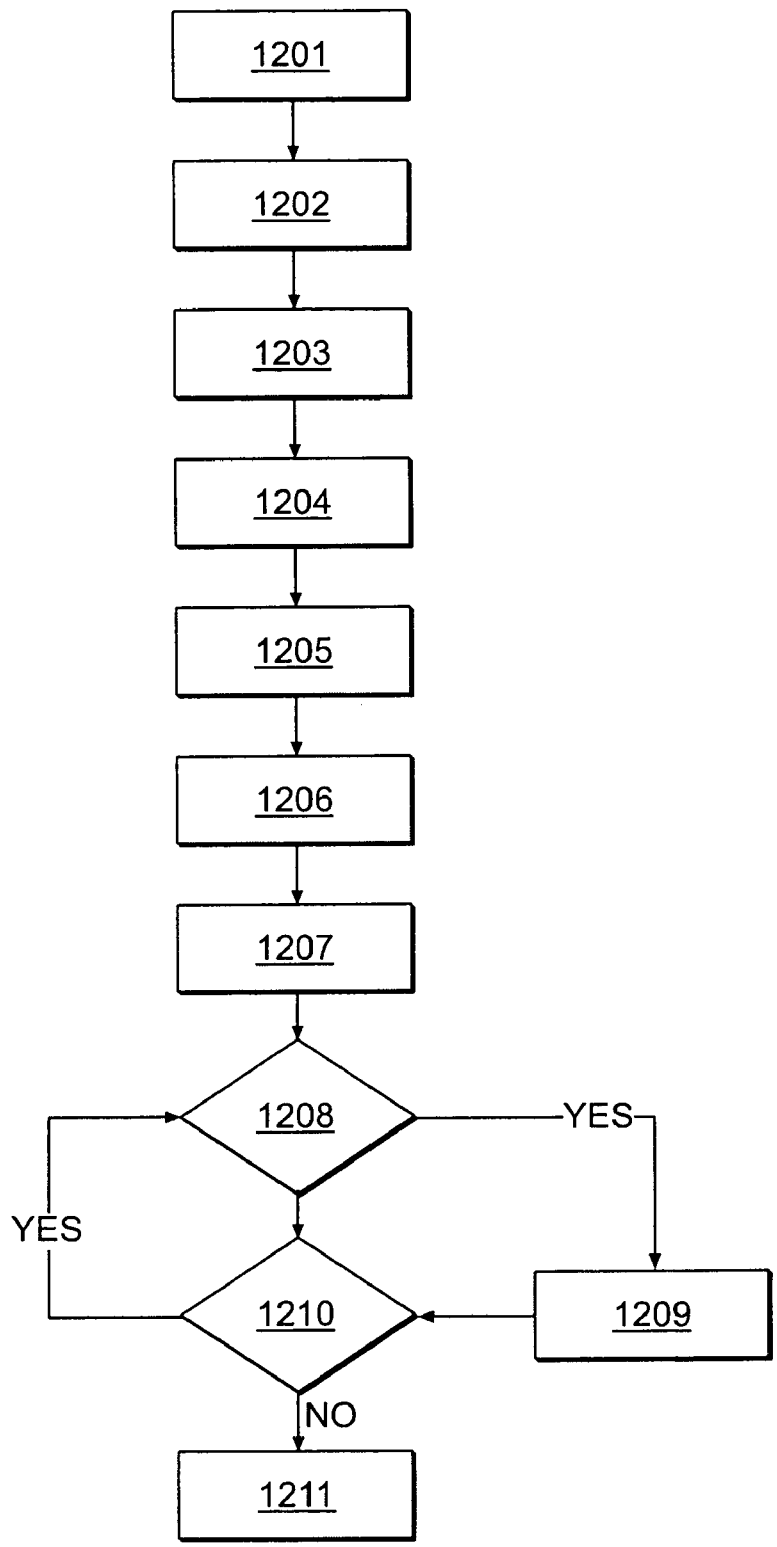
FIG. 12 is a flow chart illustrating a method for supplying a vapor and carrier gas mixture according to principles of the invention.

FIG. 12 is a flowchart describing a method for vaporizing a fluid and combining the resulting vapor with a carrier gas according to an embodiment of the invention. The steps described in the method are exemplary in nature. Further, steps may be omitted, additional steps may be added, and/or steps may be performed in a different order.

As shown in FIG. 12, the method includes providing various pieces of equipment at step 1201. Various aspects of providing equipment are described in greater detail in FIG. 13 below. A carrier gas is provided in a carrier gas line at step 1202. Fluid from a fluid source is supplied to a reservoir by adjusting a controller at step 1203. The fluid is supplied from the reservoir to a vaporizer at step 1204 and is vaporized based on commands from the controller at step 1205. At step 1206, the vapor is released into the carrier gas line to combine with the carrier gas, and at step 1207, the controller receives a data signal from the sensor system. At step 1207, it is determined whether an adjustment is needed. If an adjustment is necessary, the fluid flow from the fluid source and/or the power supply to the vaporizer is altered at step 1209. At step 1210, it is determined whether delivery of the vapor and carrier gas mixture is complete. If delivery is complete, the system may be shut off at step 1211. If delivery is not complete, the inline vaporizer system continues to operate, and the sensor system continues to provide the controller with data signals (step 1207) and the controller continues to adjust the fluid source and the vaporizer as necessary (steps 1208 and 1209). The various steps of the flowcharts presented in FIGS. 12 and 13 will be described in greater detail, as follows.

Figure 13:
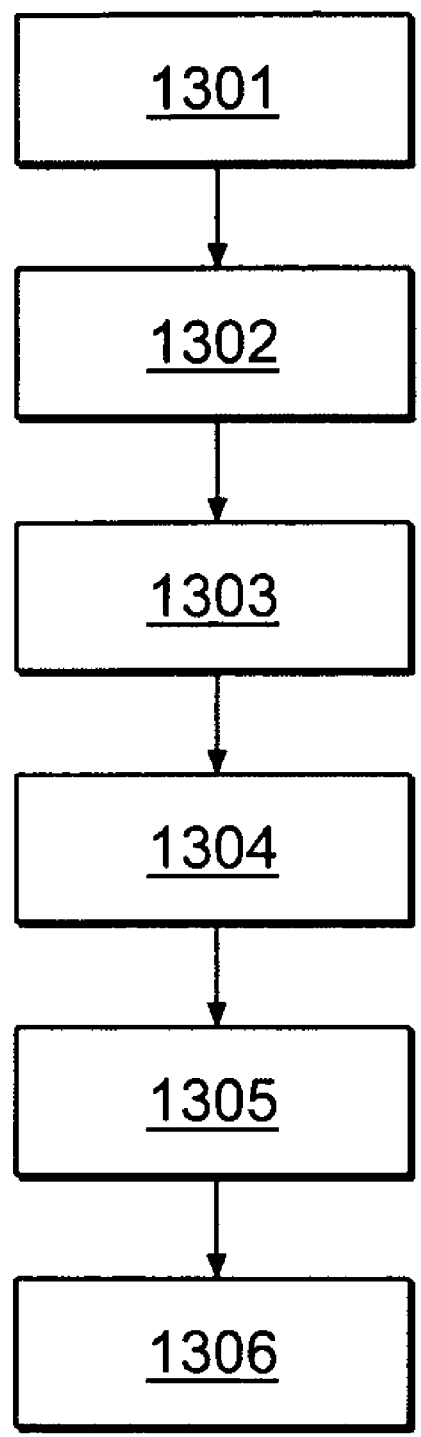
FIG. 13 is a flow chart illustrating a method for using the equipment according to principles of the invention.

The method for vaporizing a fluid and combining the resulting vapor with a carrier gas according to an embodiment of the invention includes providing equipment as shown at step 1301 in FIG. 13. As described above, various aspects of providing equipment are provided with respect to FIG. 13. FIG. 13 illustrates that a carrier gas line is provided at step 1301 and a carrier gas source is provided at step 1302. A vaporizer including a reservoir coupled with a vaporizing element may be provided in the carrier gas line at step 1303. At step 1304, a fluid source may be connected to the reservoir and a sensor system is provided in the carrier gas line at step 1305. At step 1306, a controller may be coupled with the fluid source, the vaporizer, and the sensor system. The fluid source may be positioned external to the carrier gas line and holds the fluid that will be vaporized.

A sensor system is provided in the carrier gas line, as shown at step 1305. The sensor system may be positioned at a location along the carrier gas line, at a predetermined distance from the vaporizer. This positioning of the sensor system allows it to collect data regarding temperature, flow rate, humidity of the vapor and carrier gas mixture, and/or the concentration of a drug in the vapor and carrier gas mixture, for example. A controller that is coupled with the fluid source, the vaporizer, and the sensor system is provided at step 1306.

Referring again to FIG. 12, the carrier gas is provided in the carrier gas line, as shown at step 1202. The carrier gas may be any gas that is suitable for mixing with the fluid that is vaporized, including, but not limited to air and other mixtures of gases including oxygen. At step 1203, the fluid is supplied from the fluid source to the reservoir by adjusting the controller. The fluid may include, but is not limited to, water or a drug. The fluid is supplied from the reservoir to the vaporizing element at step 1204. The vaporizing element may be, for example, a heater, a nebulizer, or a pressurized vaporizer.

At step 1205, the fluid in the vaporizer is vaporized by adjusting the vaporizer according to a command from the controller. The controller may adjust the vaporizer to achieve a desired vaporization rate. According to an embodiment of the invention, three types of controls may be employed during operation of the system. First, during steady state operation of the system, fluid is delivered based on the gas flow rate and the desired temperature and humidity. In one embodiment, the heater temperature may be controlled by a proportional, integral, derivative (PID) loop. The input gas is heated by the addition of water vapor at 100° C. or higher. The temperature of the heater may be between about 120° C. to about 150° C. while the temperature of the gas by the time it reaches the patient may be between about 33° C. and about 41° C.

In a second type of control, when the gas is too warm, the pump speed may be reduced so that less hot vapor is added to the carrier gas, thereby lowering the temperature of the gas. In third type of control, the temperature of the heater may be reduced to lower the temperature of the gas. According to an embodiment, the three types of control may be used sequentially and/or in combination to control the temperature of the gas. In another embodiment, the fluid pump flow rate may be set arbitrarily such as if the gas flow rate or temperature are not being measured or if vaporizing to ambient air. Alternatively, power to a unit may be set arbitrarily with a continuous water supply.

The vapor is released into the carrier gas line to combine with the carrier gas at step 1206 to form a vapor and carrier gas mixture, which may be provided to a patient.

At step 1207, the sensor system sends a signal to the controller regarding the data that it has collected so that the controller may adjust the fluid source and the vaporizer based on the data provided by the sensor system.

Based on the signal from the sensor system, the controller determines whether adjustment to the flow rate of the fluid or the rate of vaporization at the vaporizer is required at step 1208. If an adjustment is needed, the fluid flow to the fluid source and/or the power supply to the vaporizer may be adjusted at step 1209. For example, the instructions from the controller may increase or decrease the flow of fluid from the fluid source, or may increase or decrease the rate of vaporization at the vaporizer. Such changes may affect the temperature, flow rate, and vapor content of the resulting vapor and carrier gas mixture.

If an adjustment is not needed, the controller determines whether delivery is complete at step 1210. In addition, an operator may manually adjust the controller to terminate delivery or to suspend delivery for a specified amount of time. If delivery is completed or terminated, the operation of the system may end, as shown at step 1211. If delivery is not complete, the inline vaporizer system continues to operate and the sensor system continues to send data signals to the sensor system in 1207. Accordingly, the controller adjusts the fluid flow from the flow source to the reservoir and the power supply to the vaporizer, as shown at steps 1208 and 1209, until delivery is complete, as shown at steps 1210 and 1211.

As described above, the controller may include an alarm that alerts an operator when the delivery is complete based on durational requirements of operation, or until exhaustion of the carrier gas or fluid supply. The alarm may also be triggered by the controller based on the data signal from the sensor system. For example, if the temperature and/or vapor content of the vapor and carrier gas mixture fall out of range within a certain set of values due to a malfunction of the system, the data signal from the sensor system to the controller may prompt the inline vaporization system to shut down. This safety mechanism may prevent harm to a patient and damage to the components of the inline vaporization system.

The sensor system may also be equipped with a sensor for detecting the concentrations of contaminants in the vapor and carrier gas stream due to contaminants in the fluid or carrier gas supply or unforeseen drug interactions, for example. This chemical sensor may be designed to detect specific chemicals directly, or it may detect such contaminants through various marker chemicals. Thus, if the sensor detects an abnormally high concentration of a particular chemical contaminant, the data signal from the sensor system to the controller may prompt the inline vaporization system to shut down.

The inline vaporization system may also be equipped with a timer and an automatic shut-off that terminates operation of the system when delivery is deemed to be complete by the controller. This feature may be particularly useful if a set dosage of a drug that is supplied to the fluid source has been fully administered, as described above.

Hereinafter, the invention will be described in more detail with reference to the following examples. However, these examples are given for the purpose of illustration and are not intended to limit the scope of the invention. Tests were conducted to compare a CFV inline vaporizer system of the invention with the Conventional ventilator humidifier system illustrated in FIG. 1. The test measured both the temperature and relative humidity achieved by each system as a function of time.

Figure 14:
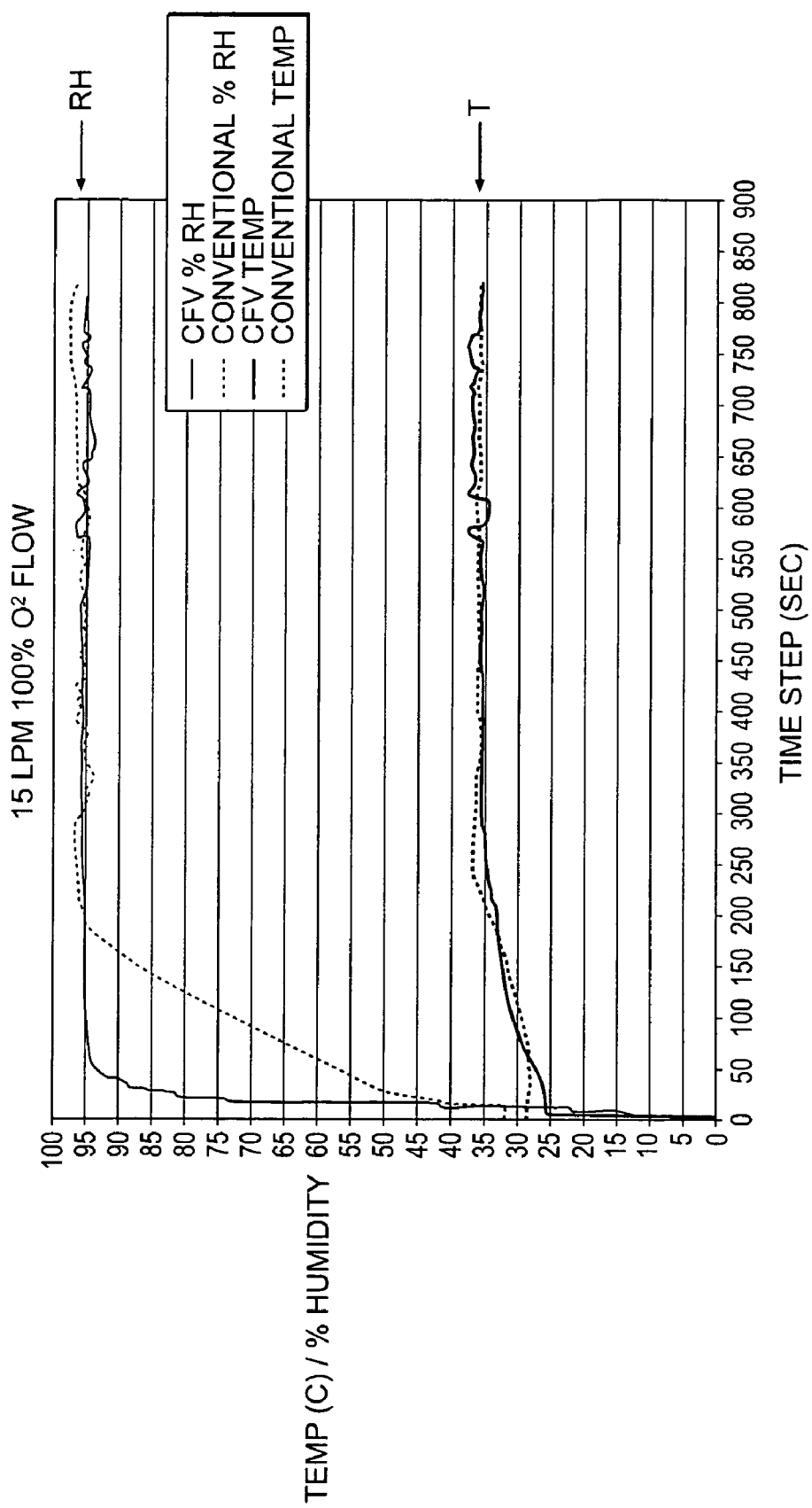
FIG. 14 is a graph of the temperature and percent humidity of a vapor and carrier gas stream as a function of time, achieved by a capillary force vaporizer (CFV) system according to principles of this invention and a Conventional ventilator humidifier system.

As shown in FIG. 14, the relative humidity in the CFV system reaches 90% after about 50 seconds of operation. In contrast, the relative humidity in the Conventional system reaches 90% after about 200 seconds from when the carrier gas flow was initiated. Moreover, this longer time for the conventional system does not include the time necessary to heat the water prior to initiation of the carrier gas flow, which may be about ten minutes or more.

Thus, the CFV system using the inline vaporizer of the invention generates vapor much earlier than the Conventional system.

Figure 15:
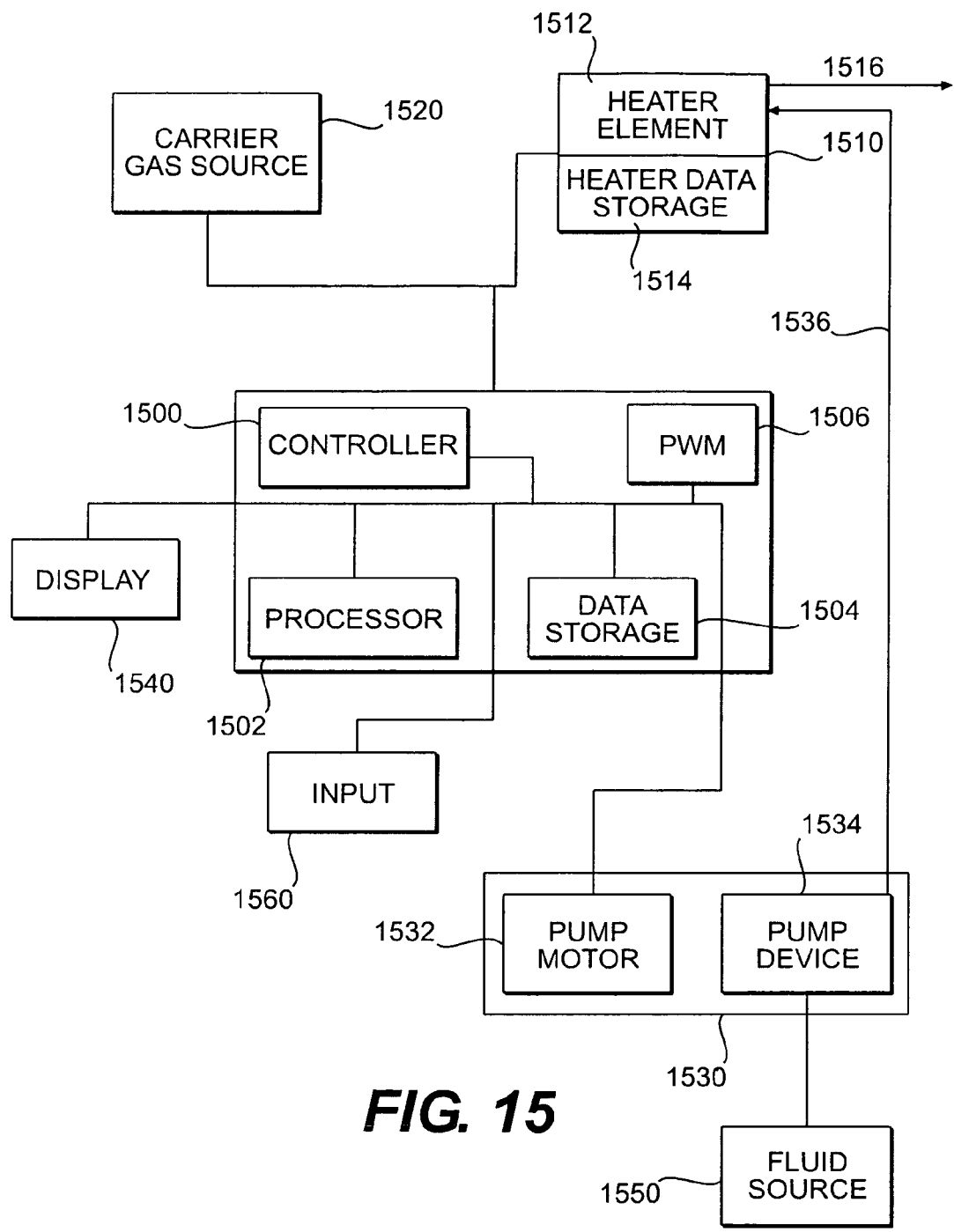
FIG. 15 illustrates a block diagram of a system for providing control of both the heater and the pump according to principles of the invention.

FIG. 15 is a block diagram of a system for providing control of both the temperature at the heater device and the rate of fluid supplied by the pump. As illustrated, controller 1500 includes a processor 1502, a storage module 1504 and a pulse width modulation (PWM) module 1506. The processor 1502, the storage module 1504 and the PWM module 1506 may be in communication with each other within controller 1500. The PWM module 1506 provides power to a heater device 1510 which can be similar to heater device 510 from FIG. 9 or a vaporizer 1170 from FIG. 11B, for example. The heater device 1510 includes a heater element 1512, a heater data storage module 1514, and an outlet 1516. As shown, the heater data storage module 1514 may be in communication with the processor 1502, the data storage module 1504, and the PWM module 1506 to allow information to be communicated between the controller 1500 and the heater fluid storage module 1514. The controller 1500 is also connected to the carrier gas source 1520 and the pump 1530. The pump 1530 may include a motor 1532, a pump device 1534, and an outlet 1536 to the heater fluid storage module 1514. The pump device 1534 is connected to a fluid source 1550. An input module 1560 allows a user to provide data to the controller 1500, while a display 1540 allows the controller 1500 to display data to a user. The operation of the controller 1500 will now be described in greater detail below.

As described above, the controller 1500 may control the temperature of the heater device, rather than control just the power supplied to the heater device 1510. The temperature at the heater device 1510 is a function of the amount of fluid, the power supplied to the heater device 1510, and the gas carrier flow. The controller 1500 receives information related to the temperature of the heater device 1510, the flow rate of the carrier gas, and the amount of fluid pumped to the heater device 1510 and controls these variables.

When a given amount of power is supplied to the heater device 1510, the temperature of the heater device 1510 will vary based on the flow of the carrier gas and the amount of fluid supplied to the heater device 1510. If the temperature of the heater device 1510 is known, the power may be adjusted to maintain the temperature when the carrier gas flow and/or the fluid flow rate are altered. Alternatively, for a given power, the temperature may be adjusted by varying the carrier gas flow rate and/or the fluid feed rate.

The temperature at the heater device 1510 may be determined using the coefficient of resistance of the heater material in the heater element 1512. At a given or baseline temperature (e.g., room temperature), the heater material has a known resistance or impedance. This resistance changes with the temperature of the heater material. The temperature at the heater surface is determined by a comparison of the impedance of the heater during usage and the impedance of the material at the baseline temperature.

Figure 16:
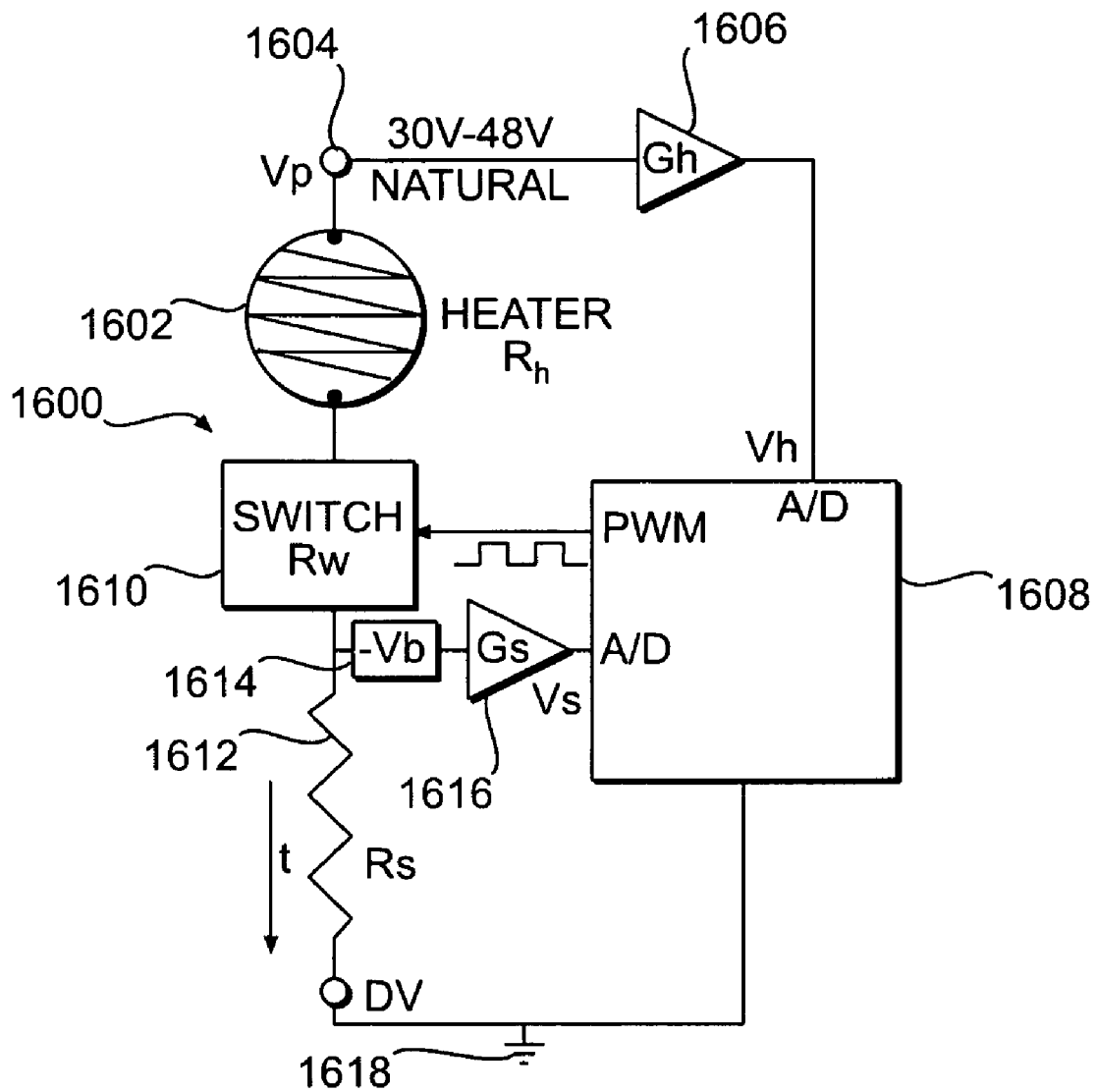
FIG. 16 is a schematic diagram of a circuit used for determining the temperature at the heater device according to principles of the invention.

FIG. 16 is a schematic diagram of a circuit 1600 used for determining the temperature at the heater device 1610 according to principles of the invention. The circuit 1600 includes a heater device 1602, with a heater material having a resistance Rh. The voltage Vp is measured at point 1604. Amplifier 1606, having a gain of Gh, provides an input to the processor 1608. A switch 1610, having a resistance of Rw, receives a PWM voltage from the processor 1608 and applies it to the heater device 1602 to control it. Feedback is provided from the switch 1610 to the processor 1608 through a bias voltage drop 1614, having a voltage drop of −Vb and an amplifier 1616, having a gain of Gs. A sense resistor 1612, having a resistance of Rs, connects the switch 1610 to ground 1618.

The controller 1600 measures the voltage across the sense resistor 1612 while the current is flowing during a PWM pulse. The PWM pulse is provided by the processor 1608. When idle, the controller 1600 measures the ambient temperature resistance and the temperature of the heater device 1510 of FIG. 15. According to an embodiment of the invention, the ambient temperature may be assumed to be 22° C. Assuming a temperature coefficient of 1500 parts per million per degree Celcius, and using a table of natural logs of resistance divided by α (0.0015), the controller may pre-compute $T_0$ via $\ln(R_0)/\alpha$ using a table look up. During steady state, another lookup is used in the same table at a later time to provide the present temperature T via $\ln(R_0)/\alpha$. T is compared to $T_0$ to determine the temperature at the heater device 1602 at steady state.

Using PID loop control, the controller 1600 uses the temperature at steady state as feedback to achieve the set point temperature. According to an embodiment of the invention, the PID loop may be designed to ramp quickly, but to avoid overshoot (e.g., causing the heater device 1510 to heat to above the desired temperature). The characteristics of various elements of the circuit 1600 are known by the design of the circuit 1600. The current flowing through resistor 1612 may be determined, thereby allowing the resistance of the heater device 1602 to be determined. Using Ohm's law to measure the circuit 1600, Vs=(iRs−Vb)Gs. Rearranging this equation results in i=(Vs+GsVb)/GsRs. As shown in FIG. 16 from using the amplifier 1606, Vh=GhVp for the measurement circuit. Also using Ohm's law for series resistance, Vp=i(Rs+Rw+Rh).

Substituting for Vp, the equation is now written as Vh/Gh=i (Rs+Rw+Rh). Substituting for i, the equation can be written as:

$$Vh/Gh=(Vs+GsVb)/GsRs(Rs+Rw+Rh) \quad (1)$$

Solving for Rh provides:

$$Rh=(VhGsRs/(Vs+GsVb)Gh)-Rs-Rw \quad (2)$$

As described previously, the resistance from temperature is determined using the equation $R=R_0 e^{(\alpha(T-T0))}$ where α=1500 ppm/degrees C. Solving for T to find the temperature from the resistance, $T=T_0+(\ln(R)/\alpha)-(\ln(R_0)/\alpha)$. Other processes for determining the temperature at the heater may also be used.

The flow rate of the carrier gas may be determined in a variety of ways. Referring back to FIG. 15, according to an embodiment of the invention, the flow rate of the carrier gas may be controlled by the carrier gas source 1520 (e.g., the ventilator). The flow rate reading from the carrier gas source 1520 may be manually input into the controller 1500 by an operator, such as a nurse or clinician. Alternatively, the controller 1500 may be in communication with the carrier gas source 1520 such that the carrier gas source 1520 transmits data including the carrier gas flow rate to the controller 1500. This transmission may occur via any known transmission, such as, but not limited to, a direct wire connection, a direct wireless transmission, or network connection with one or more components between the controller 1500 and the carrier gas source 1520. The controller 1500 receives the flow rate information from the source automatically, or as requested by the controller 1500. The controller 1500 may also be operated without having gas flow rate information by adjusting the gas temperature or by setting pump flow rate. By way of example, a ventilator may have a data output for transmitting data about the ventilator, such as the flow rate of the carrier gas. The controller 1500 may be connected to the data output of the ventilator by a wire lead. The controller 1500 receives the data about the flow rate of the carrier gas (and any other information output at the data output) from the ventilator via the wire lead.

According to another embodiment of the invention, the controller 1500 is in communication with the carrier gas source 1520, such as by a direct wire lead or by a wireless connection. The controller 1500 is set to a particular flow rate, such as by a user selecting a flow rate for the carrier gas. The controller 1500 communicates the flow rate to the gas carrier source, thereby actually controlling the carrier gas source 1520, and thus controlling the flow rate of the carrier gas.

The controller 1500 also controls the pump 1530, and more particularly the amount of fluid pumped to the heater device 1510. The pump 1530 may include a pump motor 1532 and a pump device 1534. The pump device 1534 may be positive pressure pump. According to an embodiment of the invention, the pump device 1534 may be a peristaltic pump and may be powered by a pump motor 1532, such as a stepper motor. The controller 1500 uses PWM to control the stepper motor and thus the pump.

Controller 1500 can control temperature at the heater device by controlling the pump. An open loop control may be used to control the stepper motor. The controller 1500 may also modulate the pump motor 1532 speed, and thus the pump device 1534 speed, based on the peaks and valleys associated with the ventilator's operation.

The fluid source may be a container, such as a sealed bag of water. The controller 1500 may determine the amount of fluid within the container, such as by weighing the bag. Alternatively, the amount of fluid within the container may be provided to the controller 1500, by an operator via the controller input 1560. An alert may sound when the fluid reaches a predetermined level, such as to warn the operator that the fluid is almost gone.

By knowing the amount of fluid delivered, the controller 1500 may use the carrier gas flow rate to calculate the humidity of the carrier gas delivered to the patient. More particularly, this may be done without using a sensor within the carrier gas tubing of the system. As described above, sensors may be difficult to use in determining the humidity in the carrier gas flow. In some cases, the response time for such a sensor is too slow. In addition, with some sensors, at 95% humidity or more, the sensors often over-saturate, thereby rendering the sensor ineffective. Using the amount of fluid pumped to the heater device 1510, as well as the flow rate of the carrier gas, the relative humidity of the carrier gas delivered to the patient can be determined.

A particular heating device 1510 may have information associated with it to provide for more accurate calculations. This information may include calibration information, device parameters, and recorded use, such as hours used. The information may be stored in the controller 1500 or in the memory device 1000 shown in FIG. 10 of the heater device 510. Some information, such as the recorded use, may be stored based on the interaction of the controller 1500 and the heater device 1510. Other information, such as calibration information, may be provided to the controller 1500, such as via a download from an external source. The external source may be a medium that stores the appropriate data, such as compact disc or other recordable media. Alternatively, the external source may be a computer hard drive connected to the controller, via a direct connection, through a network, or through the Internet, for example.

According to an embodiment of the invention, the heating device 1510 may have a heater data storage module 1514 for storing the information associated with the device, such as the memory device assembly 1000 described in FIG. 10. The heater data storage module 1514 may be connected to the controller 1500 and the information may be transmitted to the controller 1500 for use. In addition, the heater data storage module 1514 may be a writeable storage device that receives and stores information from the controller 1500.

As described above, it may be desirable to place a usage limit on the heating device 1510. For example, the limit may be a certain number of hours of usage (e.g., 300 hours). Alternatively, the limit may be a certain number of days (e.g., 14 days) from the first use. The controller 1500 may track the limit and cause an alert to occur when the limit has been reached or exceeded. In the case where more than one controller 1500 is used, such as when a patient is transferred or when a controller breaks down, the limit may be enforced through the use of the heater storage module 1514. If the usage limit is a certain number of hours, the controller 1500 may store information in the heater storage module 1514. If the limit is a certain number of days from the first use, the controller 1500 may cause the date of first use to be the stored in the heater storage module 1514.

Calibration information may be obtained during the initial calibration of the heater device 1510. For example, the heater device 1510 may be calibrated at the factory. Alternatively, the heater device 1510 may be calibrated when it is first hooked up, but prior to initial usage. In another alternative, the heater device 1510 may be calibrated after it has been idle for a set amount of time (e.g. five minutes). Calibration may involve determining various characteristics when the device is not in use.

The temperature at the heater device 1510 may also be determined by placing a sensor at or near the heater device 1510. The sensor may be connected to the controller 1500 and provide temperature data to the controller. Using this data, the controller 1500 may control the temperature of the heater device 1510. For example, a temperature probe may be placed at the "Y" connection in the carrier gas line near the patient. This temperature reading may be displayed at the carrier gas source. The temperature data may also be transmitted to the controller 1500 to enable a user to adjust the heater device 1510 to control the temperature of the gas carrier delivered to the patient.

While the invention has been described in terms of exemplary embodiments, those skilled in the art will recognize that the invention can be practiced with modifications in the spirit and scope of the appended claims. By way of example, the vaporizer may be used to humidify ambient air without a carrier gas line. Other arrangements may also be used.

What is claimed is:

1. A system for adding a fluid to a carrier gas comprising:
a carrier gas line for directing a carrier gas stream; and
a vaporizing device located entirely within said carrier gas line, said vaporizing device comprising a heating device having an outlet, wherein the fluid is heated to a vapor and is released at said outlet of said heating device, and wherein a carrier gas within said carrier gas line flows past said outlet of said heating device to mix and form a vapor and carrier gas mixture.

2. The system of claim 1, further comprising a fluid source connected to said heating device and operable to provide the fluid to said heating device.

3. The system of claim 1, further comprising a carrier gas source coupled with said carrier gas line and said heating device is arranged within said carrier gas line such that the carrier gas stream flows at least substantially around said heating device.

4. The system of claim 1, wherein the vapor and carrier gas mixture is delivered to a patient.

5. The system of claim 1, further comprising a controller, wherein said heating device is responsive to said controller.

6. The system of claim 5, wherein said controller includes a feedback loop to control power to said heater, wherein said power is adjusted faster than a thermal time constant of said heater.

7. The system of claim 2, further comprising a controller, wherein said fluid source is responsive to said controller.

8. The system of claim 7, further comprising a sensor located at a predetermined position along said carrier gas line, wherein said controller receives a signal from said sensor.

9. The system of claim 8, further comprising a fluid source connected to said heating device and operable to provide the fluid to said heating device, wherein said fluid source is responsive to said controller based on a signal from said sensor.

10. The system of claim 9, wherein said heating device is responsive to said controller based on a signal from said sensor.

11. The system of claim 1, wherein said vaporizing device comprises:
a porous material capillarizing the fluid; and
an orifice disk including at least one orifice proximate the heating device, wherein the capillarized fluid passes into the at least one orifice to be vaporized by the heating device.

12. The system of claim 5, wherein said controller controls at least one of a quantity of fluid delivered to said heating device, a temperature of said heating device, and a flow rate of the carrier gas.

13. The system of claim 1, wherein the carrier gas line comprises:
an air hose in fluid communication with a pump at a first end of said carrier gas line; and
a respiratory interface in fluid communication with the air hose and defining a second end of said carrier gas line.

14. A system for adding a fluid to a carrier gas, comprising:
a carrier gas source operative to generate a carrier gas flow;
a carrier gas line coupled to said carrier gas source at a first end of said carrier gas line, said carrier gas line directing carrier gas flow;
a fluid source having the fluid disposed therein;
a vaporizer coupled to said fluid source and disposed entirely within said carrier gas line, said vaporizer comprising:
an inlet receiving the fluid from said fluid source;
a converting element to convert the fluid to a vapor; and
an outlet through which the converted fluid enters the carrier gas line to mix with the carrier gas; and
a second end of said carrier gas line downstream from the vaporizer,
wherein the carrier gas flow comprises a mixture of the carrier gas and the converted fluid.

15. The system of claim 14, further comprising a controller coupled to said fluid source and operative to control the concentration of the converted fluid in the carrier gas flow downstream from said vaporizer.

16. The system of claim 14, wherein the carrier gas line comprises:
   an air hose in fluid communication with the pump at the first end of said carrier gas line; and
   a patient respiratory interface in fluid communication with the carrier gas source at the second end of said carrier gas line.

17. The system of claim 16, wherein said vaporizer is disposed proximate a connection between said air hose and said respiratory interface.

18. The system of claim 16, wherein said vaporizer is disposed proximate a junction between said air hose and said respiratory interface.

19. The system of claim 16, wherein said respiratory interface is a mask.

20. The system of claim 14, wherein said converting element is a heating element and said heating element is arranged within said carrier gas line such that the carrier gas flow flows at least substantially around said heating element.

21. The system of claim 20, wherein said vaporizer inlet comprises:
   a porous material capillarizing the fluid; and
   an orifice disk including at least one orifice proximate said converting element, wherein the capillarized fluid passes into said at least one orifice to be converted by said converting element.

22. The system of claim 14, further comprising a controller operative to control at least one characteristic of the mixture of the carrier gas and the vaporized fluid.

23. The system of claim 22, wherein said controller comprises a sensor that senses at least one of a quantity of fluid delivered to said converting element and a temperature of said heating element.

24. The system of claim 22, wherein said controller controls at least one of the quantity of fluid delivered to said converting element, the temperature of the heating element, and a flow rate of the carrier gas.

25. The system of claim 14, wherein said converting element comprises a nebulizer.

26. A humidifier ventilation system, comprising:
   a gas source providing a carrier gas flow;
   a carrier gas line having a first end coupled to said gas source, said air line directing the gas flow;
   a storage tank storing a liquid comprising at least water;
   a vaporizer disposed entirely within said carrier gas line, said vaporizer comprising:
      an inlet in fluid communication with said liquid storage tank;
      a heating element vaporizing the liquid delivered to the vaporizer via said inlet; and
      an outlet through which the vaporized liquid mixes with a gas of the carrier gas flow; and
   a second end of said carrier gas line downstream from the vaporizer,
   wherein the carrier gas flow comprises a mixture of carrier gas and the vaporized liquid.

27. The system of claim 26, wherein the carrier gas line comprises:
   an air hose in fluid communication with the pump at the first end of said carrier gas line; and
   a respiratory interface in fluid communication with the air hose at the second end of said carrier gas line.

28. The system of claim 27, wherein said vaporizer is disposed proximate a connection between said air hose and said respiratory interface.

29. The system of claim 27, wherein said vaporizer is disposed within said respiratory interface.

30. The system of claim 27, wherein said respiratory interface is a mask.

31. The system of claim 26, wherein said vaporizer inlet comprises:
   a wick comprising a porous material capillarizing the liquid; and
   an orifice disk including at least one orifice proximate said heating element, wherein the capillarized liquid passes through the at least one orifice to be vaporized by said heating element.

32. The system of claim 26, further comprising a controller regulating at least one of: a rate of the carrier gas flow from said gas source, a quantity of liquid delivered to said vaporizer from said storage tank, and a temperature of the heating element.

33. The system of claim 32, wherein said controller comprises a sensor sensing at least one of the rate of carrier gas flow, the quantity of liquid in said storage tank, and the temperature of the heating element.

34. The system of claim 32, wherein said controller comprises:
   a first input coupled with a first sensor sensing the temperature of said heating element; and
   a second input coupled with a second sensor sensing the rate of the carrier gas flow,
   wherein said controller determines a concentration of vaporized liquid in said carrier gas flow based on said first and second inputs.

35. The system of claim 26, wherein said carrier gas line comprises a holding portion that holds said heating element within said carrier gas line such that the carrier gas flow flows at least substantially around said heating element.

* * * * *